United States Patent
Kellner et al.

(10) Patent No.: US 9,151,743 B2
(45) Date of Patent: Oct. 6, 2015

(54) USE OF EEF1A AS BIOMARKER AND A METHOD OF SCREENING METAP2 INHIBITORS

(75) Inventors: Roland Kellner, Heppenheim (DE); Frank Zenke, Darmstadt (DE); Joerg Bomke, Heidelberg (DE)

(73) Assignee: MERCK PATENT GMBH, Darmstadt (DE)

( * ) Notice: Subject to any disclaimer, the term of this patent is extended or adjusted under 35 U.S.C. 154(b) by 354 days.

(21) Appl. No.: 13/127,834

(22) PCT Filed: Oct. 5, 2009

(86) PCT No.: PCT/EP2009/007102
§ 371 (c)(1),
(2), (4) Date: May 5, 2011

(87) PCT Pub. No.: WO2010/051882
PCT Pub. Date: May 14, 2010

(65) Prior Publication Data
US 2011/0275088 A1    Nov. 10, 2011

(30) Foreign Application Priority Data
Nov. 6, 2008    (EP) .................................... 08019432

(51) Int. Cl.
*G01N 33/50* (2006.01)
*C12Q 1/37* (2006.01)

(52) U.S. Cl.
CPC .............. *G01N 33/5017* (2013.01); *C12Q 1/37* (2013.01); *G01N 2333/948* (2013.01); *G01N 2800/52* (2013.01)

(58) Field of Classification Search
None
See application file for complete search history.

(56) References Cited

U.S. PATENT DOCUMENTS

2001/0034455 A1 * 10/2001 Liu et al. ....................... 549/551
2005/0032221 A1 *  2/2005 Chang et al. .................. 435/456

FOREIGN PATENT DOCUMENTS

WO    WO 03060464       7/2003

OTHER PUBLICATIONS

Li et al., Evidence That the Human Homologue of a Rat Initiation Factor-2 Associated Protein (p67) Is a Methionine Aminopeptidase; Biochem Biophys Res Comm, vol. 227, pp. 152-159, 1996.*
Moerschell et al., The Specificities of Yeast Methionine Aminopeptidase and Acetylation of Amino-terminal Methionine in Vivo; JBC, vol. 265, No. 32, pp. 19638-19643, 1990.*
Rao et al., Structure of the amino-terminal end of mammalian elongation factor Tu; NAR, vol. 14, No. 5, p. 2409, 1986.*
Thiele et al., Elongation Factor Ia from Saccharomyces cerevisiae; Rapid Large-Scale Purification and Molecular Characterization*; JBC, vol. 260, No. 5, pp. 3084-3089, 1985.*
Grant A G et al: "Differential Screening of a Human Pancreatic Adenocarinoma .Lambda.GT11 Expression Library Has Identified Increased Transcription of Elongation Factor EF-I.Alpha. In Tumour Cells" International Journal of Cancer, John Wiley & Sons, Inc, United States, Switzerland, Germany, vol. 50, No. 5, Jan. 1, 1992, pp. 740-745, XP008067884 ISSN: 0020-7136.
Scandurro A B et al: "Gene Microarray Analysis Reveals a Novel Hypoxia Signal Transduction Pathway in Human Hepatocellular Carcinoma Cells" International Journal of Oncology, Demetrios A. Spandidos Ed. & Pub, GR, vol. 19, No. 1, Jul. 1, 2001, pp. 129-135, XP009016400 ISSN: 1019-6439.
Talapatra S et al: "Elongation factor-1 alpha is a selective regulator of growth factor withdrawal and ER stress-induced apoptosis." Cell Death and Differentiation Aug. 2002, vol. 9, No. 8, Aug. 2002, pp. 856-861, XP002561429 ISSN: 1350-9047.
Hou Li et al: "Fumagillin inhibits colorectal cancer growth and metastasis in mice: in vivo and in vitro study of anti-angiogenesis." Pathology International Jul. 2009, vol. 59, No. 7, Jul. 2009, pp. 448-461, XP002561430 ISSN: 1440-1827.
Wang Jieyi et al: "Correlation of tumor growth suppression and methionine aminopetidase-2 activity blockade using an orally active inhibitor." Proceedings of the National Academy of Sciences of the United States of America Feb. 12, 2008, vol. 105, No. 6, Feb. 12, 2008, pp. 1838-1843, XP002561431 ISSN: 1091-6490.
Warder Scott E et al: "Discovery, identification, and characterization of candidate pharmacodynamic markers of methionine aminopeptidase-2 inhibition." Journal of Proteome Research Nov. 2008, vol. 7, No. 11, Oct. 2, 2008, pp. 4807-4820, XP002561432 ISSN: 1535-3893.
International Search Report of PCT/EP2009/007102 (Jan. 12, 2010).
S.E. Warder et al., "Discovery, Identification, and Characterization of Candidate Pharmacodynamic Markers of Methionine Aminopeptidase-2 Inhibition", Journal of Proteome Research, vol. 7 (2008) pp. 4807-4820.
J. Wang et al., "Correlation of Tumor Growth Suppression and Methionine Aminopetidase-2 Activity Blockade Using an Orally Active Inhibitor", PNAS, vol. 105, No. 6 (Feb. 12, 2008) pp. 1838-1843.
L. Hou et al., "Fumagillin Inhibits Colorectal Cancer Growth and Metastasis in Mice: In Vivo and In Vitro Study of Anti-Angiogenesis", Pathology International, vol. 59 (2009) pp. 448-461.

(Continued)

*Primary Examiner* — Jennifer Dunston
*Assistant Examiner* — Addison D Ault
(74) *Attorney, Agent, or Firm* — Miller, White, Zelano, Branigan, P.C.

(57) ABSTRACT

The invention relates to a method for screening compounds, which inhibit MetAP2 activity, by providing a cellular system or a sample thereof being capable of expressing MetAP2 and/or EEF1A, incubating at least a portion of the system with compounds to be screened, and detecting MetAP2 inhibition by determining EEF1A with N-terminal methionine residue (MetEEF1A). Another object of the invention concerns a method for monitoring physiological and/or pathological conditions, which are caused, mediated and/or propagated by MetAP2 activity, by administering an effective amount of at least a single compound to a mammal in need of such treatment and determining MetEEF1A in a biological sample withdrawn from the mammal. The invention also relates to the use of EEF1A as biomarker.

5 Claims, 8 Drawing Sheets

(56) References Cited

OTHER PUBLICATIONS

S. Talapatra et al., "Elongation Factor-1 Alpha is a Selective Regulator of Growth Factor Withdrawal and ER Stress-Induced Apoptosis", Cell Death and Differentiation, vol. 9 (2002) pp. 856-861.

A.B. Scandurro et al., "Gene Microarray Analysis Reveals a Novel Hypoxia Signal Transduction Pathway in Human Hepatocellular Carcinoma Cells", International Journal of Oncology, vol. 19 (2001) pp. 129-135.

A.G. Grant et al., "Differential Screening of a Human Pancreatic Adenocarcinoma gt11 Expression Library Has Identified Increased Transcription of Elongation Factor EF-1a in Tumour Cells", Int. J. Cancer, vol. 51 (1992) pp. 740-745.

\* cited by examiner

```
              10         20         30         40         50         60         70         80
P68104.pro    MGKEKTHINIVVIGHVDSGKSTTTGHLIYKCGGIDKRTIEKFEKEAAEMGKGSFKYAWVLDKLKAERERGITIDISLWKF  80
q05639.pro    MGKEKTHINIVVIGHVDSGKSTTTGHLIYKCGGIDKRTIEKFEKEAAEMGKGSFKYAWVLDKLKAERERGITIDISLWKF  80

90         100        110        120        130        140        150        160
P68104.pro    ETSKYYVTIIDAPGHRDFIKNMITGTSQADCAVLIVAAGVGEFEAGISKNGQTREHALLAYTLGVKQLIVGVNKMDSTEP  160
q05639.pro    ETTKYYITIIDAPGHRDFIKNMITGTSQADCAVLIVAAGVGEFEAGISKNGQTREHALLAYTLGVKQLIVGVNKMDSTEP  160

170        180        190        200        210        220        230        240
P68104.pro    PYSQKRYEEIVKEVSTYIKKIGYNPDTVAFVPISGWNGDNMLEPSANMPWFKGWKVTRKDGNASGTTLLEALDCILPPTR  240
q05639.pro    AYSEKRYDEIVKEVSAYIKKIGYNPATVPFVPISGWHGDNMLEPSPNMPWFKGWKVERKEGNASGVSLLEALDTILPPTR  240

250        260        270        280        290        300        310        320
P68104.pro    PTDKPLRLPLQDVYKIGGIGTVPVGRVETGVLKPGMVVTFAPVNVTTEVKSVEMHHEALSEALPGDNVGFNVKNVSVKDV  320
q05639.pro    PTDKPLRLPLQDVYKIGGIGTVPVGRVETGILRPGMVVTFAPVNITTEVKSVEMHHEALSEALPGDNVGFNVKNVSVKDI  320

330        340        350        360        370        380        390        400
P68104.pro    RRGNVAGDSKNDPPMEAAGFTAQVIILNHPGQISAGYAPVLDCHTAHIACKFAELKEKIDRRSGKKLEDGPKFLKSGDAA  400
q05639.pro    RRGNVCGDSKSDPPQEAAQFTSQVIILNHPGQISAGYSPVIDCHTAHIACKFAELKEKIDRRSGKKLEDNPKSLKSGDAA  400

410        420        430        440        450        460
P68104.pro    IVDMVPGKPMCVESFSDYPPLGRFAVRDMRQTVAVGVIKAVDKKAAGAGKVTKSAQKAQKA-K              462
q05639.pro    IVEMVPGKPMCVESFSQYPPLGRFAVRDMRQTVAVGVIKNVEKKSGGAGKVTKSAQKAQKAGK              463
```

Decoration 'Decoration #1': Box residues that match the Consensus exactly.

Figure 11

USE OF EEF1A AS BIOMARKER AND A METHOD OF SCREENING METAP2 INHIBITORS

SEQUENCE LISTING

The instant application contains a Sequence Listing which has been submitted in ASCII format via EFS-Web and is hereby incorporated by reference in its entirety. Said ASCII copy, created on Jul. 8, 2011, is named MERCK383.txt and is 9,031 bytes in size.

The invention relates to a method for screening compounds, which inhibit MetAP2 activity, by providing a cellular system or a sample thereof being capable of expressing MetAP2 and/or EEF1A, incubating at least a portion of the system with compounds to be screened, and detecting MetAP2 inhibition by determining EEF1A with N-terminal methionine residue (MetEEF1A). Another object of the invention concerns a method for monitoring physiological and/or pathological conditions, which are caused, mediated and/or propagated by MetAP2 activity, by administering an effective amount of at least a single compound to a mammal in need of such treatment and determining MetEEF1A in a biological sample withdrawn from the mammal. The invention also relates to the use of EEF1A as biomarker.

Prokaryotic and eukaryotic protein synthesis is initiated with an AUG codon that specifies an N-terminal methionine. In the majority of cellular proteins, the methionine is removed cotranslationally, and this removal of the initiator methionine is required for proper function of these proteins, i.e. activity, localization, and stability. N-terminal methionine processing is accomplished by the action of two intracellular metalloproteases: methionine aminopeptidase 1 and 2 (MetAP1 and MetAP2). MetAP1 and MetAP2 are dissimilar in a number of key respects. These include substrate specificity and expression control. For example, MetAP2 is able to process a limited set of proteins untouched by MetAP1. In addition, induction of MetAP2 expression is associated with cell proliferation, whereas MetAP1 is constitutively expressed. More recently, MetAP1 has been shown to play a role in the G2/M phase of cell cycle, whereas MetAP2 inhibition leads to G1 arrest.

The biological role of MetAP2 is not well understood, however, the enzyme plays an important role in embryonic development and vasculogenesis, and the inhibition of enzymatic activity is regarded as an attractive approach for cancer therapy. The natural product fumagillin and its analog TNP-470 selectively block MetAP2 activity and inhibit endothelial cell proliferation. Although the anti-angiogenic compound TNP470 inhibits MetAP2 potently and irreversibly, its therapeutic use is limited due to significant toxicity. Further knowledge on substrate interactions may help to explain anti-angiogenic and anti-tumoral effects of MetAP2 inhibitors.

It has been recently postulated, that drug-sensitive cells may have specific MetAP2 substrates that cannot be processed by the type 1 enzyme. Several approaches were therefore taken to determine whether cells treated with the drugs have specific defects in methionine processing. Fumagillin, TNP-470 and A-832234 were used in cell-based assays to study the inhibition of MetAP2 and to identify novel and robust marker proteins for MetAP2 inhibition.

The housekeeping protein glyceraldehyde-3-phosphate dehydrogenase (GAPDH) was detected after selective inhibition of methionine processing nearly a decade ago. An initial assay for the active cellular MetAP2 enzyme is known from Turk et al. (1999) Chem & Biol 6: 823-833, which is based on the 2D gel mobility shift of the enzyme GAPDH from cells treated with TNP-470. The assay can only be used for irreversible MetAP2 inhibitors. Wang et al. (2008) PNAS 105(6): 1838-1843, initiated efforts to establish an assay to differentiate GADPH variants with unprocessed N-terminal methionine from mature processed GAPDH by speculating that 1D isoelectric-focusing electrophoresis (IEF) might separate the GAPDH variants with and without N-terminal methionine, and that IEF followed by immunoblot might provide an assay for GAPDH variants as a marker for cellular MetAP2 inhibition. However, GAPDH was identified in treated as well as untreated HCT-116 human colon carcinoma cells with an N-terminal sequence lacking methionine. Up to now, no reliable and robust detection system could be established to monitor this putative marker.

Prior art also described the detection of the protein 14-3-3γ as a biomarker for MetAP2 (WO 2002/39990 A2). The 14-3-3γ isoform was reported to be induced when a MetAP inhibitor compound is applied to mammalian cells. It belongs to the family of 14-3-3 proteins. The specific detection of 14-3-3γ isoform is hampered by the fact that the related isoforms show very similar properties in protein analytical studies, and even more specifically, an altered 14-3-3γ isoform needs to be detected Therefore, the technical problem forming the basis of the present invention is to provide a method for screening compounds, which effectively inhibit the proteolytic activity of MetAP2. It is another problem of the invention to provide a biomarker, which allows the identification and characterization of the MetAP2 inhibiting properties of such compounds in-vitro and in-vivo. It is still another problem to provide substances for the detection of altered MetAP2 activity, which makes a simple and fast monitoring of proliferative-dependent diseases possible.

The present invention solves the problem by providing a method for screening compounds, which inhibit methionine aminopeptidase 2 (MetAP2) activity, comprising the steps of:
 (a) providing a cellular system or a sample thereof being capable of expressing MetAP2 and/or eukaryotic translation elongation factor 1 alpha (EEF1A), wherein the system is selected from the group of single cells, cell cultures, tissues, organs and mammals,
 (b) incubating at least a portion of the system with compounds to be screened, and
 (c) detecting MetAP2 inhibition by determining EEF1A with N-terminal methionine residue (MetEEF1A).

It has been surprisingly demonstrated by the inventors that the protein EEF1A is a substrate for MetAP2, but it appears not to be processed by MetAP1. Consequently, the aforementioned EEF1A protein represents a novel biomarker that is well suited for monitoring the level of MetAP2 activity. The underlying biomarker EEF1A of the invention has been unexpectedly found to be differentially processed after cell-based studies using MetAP2 inhibitors. Since the initiator methionine of EEF1A is not cleaved off after pharmacological MetAP2 inhibition, the protein carries an N-terminal methionine instead of an acetylated glycine residue.

The protein EEF1A has already been described in the state of the art by sequence and other features; however, a link to MetAP2 has not been identified previously. The eukaryotic translation elongation factor 1 alpha (EEF1A) is a 50 kD cytoplasmic protein of the GTP-binding elongation factor family (EF-Tu/EF-1A subfamily). The factor is involved in protein biosynthesis and especially found in a nuclear export complex that is composed of Exportin-5 (XPO5), EEF1A1, Ran and aminoacylated tRNA. The interaction with XPO5 promotes the GTP-dependent binding of aminoacyl-tRNA to the A-site of ribosomes. The aforementioned protein EEF1A may be named in another way, such as eEF1A, EF1A, EF1α, EF1alpha, EF1a, leukocyte receptor cluster member 7 (LENG7) and elongation factor Tu (EF-Tu). It shall be considered that EF-Tu is actually a protein of another structure and function.

EEF1A comprises a group of different proteins EEF1A1, EEF1A2, etc., which are subsumed under the scope of protection. Both explicitly mentioned isoforms have identical N-termini and are especially applicable in the method of the invention. Reference to a specified EEF1A isoform shall not be understood to limit the scope of protection since the protein members of the group represented by EEF1A may be replaced by each other. The teaching of the present specification concerning a specific EEF1A isoform, such as EEF1A1, is considered as valid and applicable without restrictions to other members of the EEF1A group if expedient therein. It is also not excluded that further EEF1A isoforms will be characterized, which also exhibit a high homology to some or even all members of the EEF1A group, particularly at the N-terminus, as well as a strong substrate affinity to MetAP2. Therefore, the teaching of the present invention is not restricted to the currently known EEF1A isoforms, but shall cover each EEF1A isoform of high homology to them and strong substrate affinity to MetAP2. The isoforms of EEF1A can be easily assigned by the accession numbers (e.g. P68104, Q05639), which are generally accepted and fixed in numerous data bases, such as the GenBank, SwissProt and the like.

In the first step (a), a cellular system is provided. The cellular system is defined to be any subject provided that the subject comprises cells. Hence, the cellular system can be selected from the group of single cells, cell cultures, tissues, organs and mammals. The scope of the cellular system also comprises parts of such biological entities, i.e. samples of tissues, organs and mammals. It shall be understood that each cellular system in the aforementioned order represents a sample of the respective following system.

Particularly, the cellular sample is taken in-vivo or in-situ from a mammal to be tested. The withdrawal of the cellular sample follows good medical practice. Biological samples may be taken from any kind of biological species, but the sample is especially taken from a laboratory animal or a human, more preferably a rat, mouse or human, most preferably a human.

In the present invention, the cellular system may also comprise a biological fluid, wherein the sample of body fluid preferably consists of blood, serum, plasma, saliva or urine. It is also preferred to gather a tissue sample by biopsy, especially taken close to the location of ailment. The biological samples can be originated from any tissue, such as the uterus, pituitary gland, liver, brain, colon, breast, adipose tissue, etc. The sample may be purified to remove disturbing substances, such as inhibitors for the formation of hydrogen bonds.

The cell sample refers to any type of primary cells or genetically engineered cells, either in the isolated status, in culture or as cell line, provided that they are capable of expressing MetAP2 and/or EEF1A, preferably MetAP2 and EEF1A. Although it is particularly preferred that the cells are capable of expressing MetAP2, it shall be not excluded that MetAP2-deficient cells can be used and the enzyme MetAP2 is artificially added to the cellular system. Although it is also particularly preferred that the cells are capable of expressing EEF1A, it shall be not excluded that EEF1A-deficient cells can be used and EEF1A is artificially added to the cellular system. The assay of the invention can be even completely performed in-vitro, i.e. the cellular system of step (a) according to the invention can be waived. Hence, step (a) is modified such that an amount of isolated MetAP2 is provided in crude of purified form.

It shall also be understood that variants, mutants, parts or homologous protein sequences of MetAP2 having the same function, are included in the scope of definition as well as protection. The degree of alteration between the original sequence and its derivatives is inevitably limited by the requirement of substrate recognition and methionine cleavage. Preferably, the homology amounts to at least 85%, more preferably at least 95%, most preferably at least 98%. Possible alterations comprise deletion, insertion, substitution, modification and addition of at least one amino acid, or the fusion with another protein acid. The engineered cells are capable of expressing the MetAP2 protein by transfection with appropriate vectors harboring the corresponding gene or parts thereof. Preferably, the recombinant cells are of eukaryotic origin.

The prior teaching concerning MetAP2 alterations is considered to be valid and applicable without restrictions to EEF1A alterations if expedient. As obvious to the skilled artisan, the present invention shall not be construed to be limited to the full-length protein EEF1A of SEQ ID NOs: 1 and 2 (cf. FIG. 11). Physiological or artificial fragments of EEF1A, secondary modifications of EEF1A, species-dependent alterations as well as allelic variants of EEF1A are also encompassed by the present invention. In this regard an "allelic variant" is understood to represent the gene product of one of two or more different forms of a gene or DNA sequence that can exist at a genetic single locus. Artificial fragments preferably encompass a peptide produced synthetically or by recombinant techniques, which at least comprises the N-terminus of diagnostic interest consisting of at least the N-terminal 20 contiguous amino acids as derived from the sequence disclosed in SEQ ID NOs: 1 or 2, preferably at least the N-terminal 40 contiguous amino acids, more preferably at least the N-terminal 60 contiguous amino acids, highly preferably at least the N-terminal 82 contiguous amino acids. It is particularly preferred that such N-terminal fragments or the N-terminus of full-length proteins, wherein the length of their N-terminus is defined in accordance with the N-terminal fragments, exhibit a complete identity to the corresponding N-termini of the proteins according to SEQ ID NOs: 1 and 2 in order to ensure substrate recognition at all. Such a fragment may be advantageously used as a standard in an immunoassay. Preferably, full-length EEF1A or a physiological variant of this marker is detected in a method according to the present invention.

In a more preferred embodiment of the present invention, a cell line is provided in step (a) of the screening method. Most preferred cell lines of the present invention are mouse brain endothelioma cells (bEND.3), human colon carcinoma cells (HCT116), human umbilical vein endothelial cells (HUVEC) and/or human fibrosarcoma cells (HT1080).

The cell sample is stored, such as frozen, cultivated for a certain period or immediately subjected to step (b). Before incubating it with compounds to be screened, the cell sample is divided into multiple portions. At least two portions are provided; one is used for screening while the other one serves as control. Preferably, the number of portions for screening exceeds the number of control portions. Usually, numerous portions are subjected to a high-throughput screening.

As used herein, a "compound with MetAP2 inhibiting activity" is an agent that blocks at least some of the biological effects of MetAP2, which refers to any factor, agent, compound whether endogenous or exogenous in origin, which is capable of binding and interacting with MetAP2 and thereby stopping certain biological effects of MetAP2. The skilled artisan would know that, for instance, one of the biological effects of MetAP2 is to promote cell proliferation.

The compounds are composed of biological and/or chemical structures capable to interact with a target molecule. Herein, any component of MetAP2 signaling shall be considered as "target molecule", which is not limited to the MetAP2 protein target, but may also comprise the coding gene or a gene product thereof, or a regulator protein, or a component of a signal transduction pathway comprising said gene or gene products thereof. Consequently, the specific interaction of compounds may involve either the mere targeting or the induction of alterations in cell function, or it may even include both effects simultaneously.

The compounds to be screened in the inventive method are not restricted anyway. In particular, the compounds are selected from the group of nucleic acids, peptides, carbohydrates, polymers, small molecules having a molecular weight between 50 and 1.000 Da and proteins. These compounds are often available in libraries. It is preferred to incubate a single compound within a distinct portion of the cell sample. However, it is also possible to investigate the cooperative effect of compounds by incubating at least two compounds within one portion. A further portion of cells is simultaneously incubated in the absence of the compounds.

The term "incubation" denotes the contacting of the compounds with the cells for a distinct period, which depends on the kind of compounds and/or target. The incubation process also depends on various other parameters, e.g. the cell type and the sensitivity of detection, which optimization follows routine procedures known to those skilled in the art. The incubation procedure can be realized without a chemical conversion or may involve a biochemical reaction. Adding chemical solutions and/or applying physical procedures, e.g. impact of heat, can improve the accessibility of the target structures in the sample. Specific incubation products are formed as result of the incubation.

In step (c), the identification of effective compounds in the meaning of the invention is indirectly performed by determining the presence of EEF1A with N-terminal methionine. The determination is performed at a specified moment and correlated to the signal strength at the beginning of the experiment and the positive/negative control. Either the control system is not incubated with the compounds (negative control) or the control system is incubated with a standard compound having no MetAP2 inhibiting activity (negative control) or a standard compound having MetAP2 inhibiting activity (positive control). The activity is revealed by a change in protein processing, i.e. the initiator methionine is not cleaved off after treatment with a potentially inhibiting compound. Pair-wise comparisons are made between each of the treatments. A pair-wise comparison involves the protein processing data for the given biomarker EEF1A under a given treatment condition compared to the protein processing data for this protein under a second treatment condition. The comparison is performed using suitable statistical technique with the assistance of known and commercially available programs.

The detection may be performed by applying the intact cell to a detection method of choice. It is preferred, however, to provide cellular extracts first. Cell lysis can be performed in suitable, well-known lysis buffers, which may cause an osmotic shock and perforate the cell membrane. The stability of the cell structure can also be destroyed by mechanical forces, such as ball mill, French press, ultrasonic, etc., by enzymatic degradation of cell wall and cell membrane, respectively, and/or by the action of tensides. The biomarker may be further purified to remove disturbing substances or the biomarker EEF1A can be concentrated in the sample. Downstream-processing and/or concentrating are preferably performed by the method of precipitation, dialysis, gel filtration, gel elution, or chromatography, such as HPLC or ion exchange chromatography. It is recommended to combine several methods for better yields.

Suitable tests for detecting MetAP2 inhibition are known to those skilled in the art or can be easily designed as a matter of routine. Many different types of assays are known, examples of which are set forth below. Although the assay according to the invention may be any assay suitable to detect and/or quantify gene expression, MetEEF1A is preferably determined by means of substances specifically interacting with MetEEF1A.

The term "specific substances" as used herein comprises molecules with high affinity to at MetEEF1A in order to ensure a reliable binding. The substances are preferably specific to parts of the protein. Such parts represent a restriction to those regions which are sufficient for the expression of a specific function, i.e. the provision of a structural determinant for recognition. All truncations are inevitably limited by the requirement of preserving the unique recognition. However, the parts of the gene products can be very small. Preferably, the substances are mono-specific in order to guarantee an exclusive and directed interaction with the chosen single target. It is particularly required that the specific substances are capable of discriminating between EEF1A (e.g. a protein with an acetylated glycine residue at the N-terminus) and MetEEF1A (i.e. protein with a methionine residue at the N-terminus).

The recognition of the protein or N-terminal parts thereof according to the invention can be realized by a specific interaction with substances on the primary, secondary and/or tertiary structure level of an amino acid sequence. The single amino acid modification at the N-terminus favors the primary structure recognition. In the context of the present invention, the term "recognition"—without being limited thereto—relates to any type of interaction between the specific substances and the target, particularly covalent or non-covalent binding or association, such as a covalent bond, hydrophobic/hydrophilic interactions, van der Waals forces, ion pairs, hydrogen bonds, ligand-receptor interactions, interactions between epitope and antibody binding site, nucleotide base pairing, and the like. Such association may also encompass the presence of other molecules such as peptides, proteins or other nucleotide sequences.

The specific substances are composed of biological and/or chemical structures capable to interact with the target molecule in such a manner that makes a recognition, binding and interaction possible. In particular, the substances are selected from the group of nucleic acids, peptides, carbohydrates, polymers, small molecules having a molecular weight between 50 and 1.000 Da and proteins, preferably nucleic acids and proteins. The specific substances express a sufficient sensitivity and specificity in order to ensure a reliable detection. A specific substance has at least an affinity of $10^{-7}$ M for its corresponding target molecule. The specific substance preferably has an affinity of $10^{-8}$ M or even more preferred of $10^{-9}$ M for its target molecule. As the skilled artisan will appreciate the term specific is used to indicate that other biomolecules present in the sample do not significantly bind to the substance specific for MetEEF1A. Preferably, the level of binding to a biomolecule other than the target molecule results in a binding affinity of only 10% of the affinity of the target molecule, more preferably only 5% or less. A most preferred specific substance will fulfill both the above minimum criteria for affinity as well as for specificity.

The proteins or peptides are preferably selected from the group consisting of antibodies, cytokines, lipocalins, receptors, lectins, avidins, lipoproteins, glycoproteins, oligopeptides, peptide ligands and peptide hormones. More preferably, antibodies are used as specific substance. "Antibody" denotes a polypeptide essentially encoded by an immunoglobulin gene or fragments thereof. According to the invention, antibodies are present as intact immunoglobulins or a number of well-characterized fragments. Fragments are preferably selected from the group consisting of $F_{ab}$ fragments, $F_c$ fragments, single chain antibodies (scFv), variable regions, constant regions, H chain ($V_H$), and L chain ($V_L$), more preferably $F_{ab}$ fragments and scFv. Fragments, such as $F_{ab}$ fragments and $F_c$ fragments, can be produced by cleavage using various peptidases. Furthermore, fragments can be engineered and recombinantly expressed, preferably scFv.

The term "nucleic acid" refers to a natural or synthetic polymer of single- or double-stranded DNA or RNA alternatively including synthetic, non-natural or modified nucleotides, which can be incorporated in DNA or RNA polymers. Each nucleotide consists of a sugar moiety, a phosphate moiety, and either a purine or pyrimidine residue. The nucleic acids are preferably single or double stranded DNA or RNA, primers, antisense oligonucleotides, ribozymes, DNA enzymes, aptamers and/or siRNA, or parts thereof. The nucleic acids can be optionally modified as phosphorothioate DNA, locked nucleic acid (LNA), peptide nucleic acid (PNA) or spiegelmer. Particular preferred nucleic acid probes to be used as MetAP2-specific substances are aptamers.

DNA aptamers and RNA aptamers have been found to express a high affinity for a wide variety of target molecules. Target structures may comprise proteins, peptides and small molecules, such as organic dyes, nucleotides, amino acids, vitamins, alkaloids, etc. More preferred are RNA aptamers since the 2'-hydroxyl group available in RNA promotes a couple of intra- and intermolecular contacts, the latter being between molecules of the same sequence, different sequences, or between RNA and any other molecule which is not composed of RNA. These nucleic acid ligands can be identified by an efficient in-vitro selection procedure—the so-called SELEX process (systematic evolution of ligands by exponential enrichment). Since RNA is very susceptible to nucleolytic degradation in biological solutions, RNA aptamers should be chemically modified using phosphorothioates, locked nucleic acids, or Spiegelmers, for instance. L-RNA versions of aptamers called Spiegelmers are especially long-lived as they are essentially impervious to natural degradation processes. Because of their high affinity for a broad spectrum of structural targets, aptamers act very similar to antibodies.

Aptamers can be synthesized using standard phosphoramidite chemistry. In addition, RNA aptamers having more than approximately 30 nucleotides can be favorably synthesized in large amounts by in-vitro transcription. Selection, synthesis, and purification of aptamers are well-known to those skilled in the art.

The specific substances can be labeled, in doing so the labeling depends on their inherent features and the detection method to be applied, i.e. the required sensitivity, ease of conjugation, stability requirements, and available instrumentation and disposal provisions. For the detection of specific incubation products, the applied methods depend on the specific incubation products to be monitored and are well-known to the skilled artisan. Preferred examples of suitable detection methods according to the present invention are luminescence, particularly fluorescence, furthermore VIS coloring and/or radioactive emission.

Luminescence concerns the emission of light as a result of chemiluminescence, bioluminescence or photoluminescence. Chemiluminescence involves the emission of visible light as a result of a chemical reaction, whereas bioluminescence requires the activity of luciferase. The presently preferred photoluminescence, which is also known as fluorescence stimulation, is caused by the absorption of photons, preferably provided by radiation, which is released again as photon with a shift in wavelength of 30 to 50 nm and within a period of approximately $10^{-8}$ seconds. The instruments for fluorescence detection include, but are not limited to typical benchtop fluorometers, fluorescence multi-well plate readers, fiber optic fluorometers, fluorescence microscopes and microchips/microfluidics systems coupled with fluorescence detection.

VIS coloring denotes the visualization of any achromatic substance in order to be visible to the naked eye. Preferably, the intensity of coloring is measured by a photometer. Radioactive radiation of isotopes is measured by scintillation. The process of liquid scintillation involves the detection of beta decay within a sample via capture of beta emissions in a system of organic solvents and solutes referred to as the scintillation cocktail. The beta decay electron emitted by radioactive isotopes such as $^3H$, $^{14}C$, $^{32}P$, $^{33}P$ and $^{35}S$ in the sample excites the solvent molecule, which in turn transfers the energy to the solute. The energy emission of the solute (the light photon) is converted into an electrical signal by a photo-multiplier tube within a scintillation counter. The cocktail must also act as a solubilizing agent keeping a uniform suspension of the sample. Gamma ray photons often arise as a result of other decay processes (series decay) to rid the newly formed nucleus of excess energy. They have no mass and produce little if any direct ionization by collision along their path. Gamma photons are absorbed for detection and quantization by one or more of three mechanisms: The Compton effect, the photoelectric effect and pair production. A favorable gamma decay isotope of the present invention is $^{125}I$.

A labeling method is not particularly limited as long as a label is easily detected. A "labeled specific substance" is one that is bound, either covalently through a linker or a chemical bond, or non-covalently through ionic, van der Waals, electrostatic, hydrophobic interactions or hydrogen bonds, to a label such that the presence of the MetEEF1A protein may be detected by detecting the presence of the label bound to the biomarker.

The covalent linkage of an anti-MetEEF1A antibody to an enzyme may be performed by different methods, such as the coupling with glutaraldehyde. Both, the enzyme and the antibody are interlinked with glutaraldehyde via free amino groups, and the by-products of networked enzymes and antibodies are removed. In another method, the enzyme is coupled to the antibody via sugar residues if it is a glycoprotein, such as the peroxidase. The enzyme is oxidized by sodium periodate and directly interlinked with amino groups of the antibody. Other enzyme containing carbohydrates can also be coupled to the antibody in this manner, however sometimes a loss in activity is observed due to the oxidation, e.g. a diminished activity of alkaline phosphatase. Enzyme coupling may also be performed by interlinking the amino groups of the antibody with free thiol groups of an enzyme, such as β-galactosidase, using a heterobifunctional linker, such as succinimidyl 6-(N-maleimido) hexanoate.

Specific immunological binding of an antibody to a protein can be detected directly or indirectly. Direct labels include fluorescent or luminescent tags, metals, dyes, radionuclides, and the like, attached to the antibody. An antibody labeled with iodine-125 ($^{125}$I) can be used. A chemiluminescence assay using a chemiluminescent antibody specific for the protein marker is suitable for sensitive, non-radioactive detection of protein levels. An antibody labeled with fluorochrome is also suitable. Examples of fluorochromes include, without limitation, DAPI, fluorescein, Hoechst 33258, R-phycocyanin, B-phycoerythrin, R-phycoerythrin, rhodamine, Texas red, and lissamine. Indirect labels include various enzymes well known in the art, such as horseradish peroxidase (HRP), alkaline phosphatase (AP), β-galactosidase, urease and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranosxde (ONPG), which yields a soluble product detectable at 410 nm. A urease detection system can be used with a substrate, such as urea-bromocresol purple.

In a preferred embodiment of the present invention, the antibodies are labeled with detectable moieties, which include, but are not limited to, radionuclides, fluorescent dyes, e.g. fluorescein, fluorescein isothiocyanate (FITC), Oregon Green™, rhodamine, Texas red, tetrarhodimine isothiocynate (TRITC), Cy3, Cy5, etc., fluorescent markers, e.g. green fluorescent protein (GFP), phycoerythrin, etc., auto-quenched fluorescent compounds that are activated by tumor-associated proteases, enzymes, e.g. luciferase, HRP, AP, etc., nanoparticles, biotin, digoxigenin and the like.

In another preferred embodiment of the present invention, the nucleic acids are labeled with digoxigenin, biotin, chemiluminescence substances, fluorescence dyes, magnetic beads, metallic beads, colloidal particles, electron-dense reagents, enzymes, all of them are well-known in the art, or radioactive isotopes. Preferred isotopes for labeling nucleic acids in the scope of the invention are $^3$H, $^{14}$C, $^{32}$P, $^{33}$P, $^{35}$S, or $^{125}$I, more preferred $^{32}$P, $^{33}$P, or $^{125}$I.

A variety of immunoassay techniques, including competitive and non-competitive immunoassays, can be used. The term "immunoassay" encompasses techniques including, without limitation, enzyme immunoassays (EIA), such as enzyme multiplied immunoassay technique (EMIT), enzyme-linked immunosorbent assay (ELISA), IgM antibody capture ELISA (MAC ELISA) and microparticle enzyme immunoassay (MEIA), furthermore capillary electrophoresis immunoassays (CEIA), radio-immunoassays (RIA); immunoradiometric assays (IRMA), fluorescence polarization immunoassays (FPIA) and chemiluminescence assays (CL). If desired, such immunoassays can be automated. Immunoassays can also be used in conjunction with laser induced fluorescence. Liposome immunoassays, such as flow-injection liposome immunoassays and liposome immunosensors, are also suitable for use in the present invention. In addition, nephelometry assays, in which the formation of protein/antibody complexes results in increased light scatter that is converted to a peak rate signal as a function of the marker concentration, are suitable for use in the methods of the present invention.

In an embodiment of the present invention, antibodies are used as specific substances to MetEEF1A and the incubation products are detected by the labeling of the antibodies, preferably by ELISA, RIA, fluoro immunoassay (FIA), soluble particle immune assay (SPIA) or western blotting.

In a preferred embodiment of the invention, an ELISA is used for the detection of the incubation products. Component of ELISAs are enzymes which are bound to one partner of the immunological reaction. The tracer antigen (analyte derivative) of MetEEF1A is preferably labeled in the competitive ELISA using a single capture antibody (herein after referred to as primary), whereas the antibody is preferably labeled in the non-competitive ELISA preferably comprising the precipitation of the antigen-antibody complex by a second antibody (herein after referred to as secondary) which is directed to another epitope of MetEEF1A than the primary antibody. Complexes consisting of antigen and two antibodies are also called sandwich complexes. The detection comprises the subsequent enzymatic conversion of a substrate to a product, preferably a colored product, which is recognized by visual coloring, bioluminescence, fluorescence or the measurement of electrical signals (enzyme electrode). Favorable enzymes for labeling in the present invention are known to the skilled artisan, such as peroxidase (e.g. HRP), chloramphenicol acetyl transferase (CAT), green fluorescent protein (GFP), glutathione S-transferase (GST), luciferase, β-galactosidase and AP.

Additionally preferred are radioactive immunoassays utilizing radioactive isotopes which are either incorporated into an immune reagent during synthesis, preferably into tracer MetEEF1A, or subsequently coupled to an immune reagent of the assay, preferably to an antibody. Preferred radioactive isotopes in the inventive method are $^3$H, $^{14}$C, $^{32}$P, $^{33}$P, $^{35}$S, and $^{125}$I, and more preferred $^{14}$C, $^{35}$S, and $^{125}$I. A favorite method follows the competitive principle of binding. A constant amount of radioactive MetEEF1A and a variable amount of MetEEF1A marker of the sample to be analyzed compete for a defined amount of antibody which is present in excess. The displacement of tracer is directly proportional to the marker concentration which can be evaluated by a calibration curve.

Antigens or antibodies, respectively, which are favorably labeled with fluorophores, are used in FIAs.

SPIA utilizes the color change of silver particle as result of agglutination. Neither a secondary antibody nor an indicator reaction are required making it particularly useful in the scope of the present invention. Similarly favorably is the latex agglutination test using antibodies which are bound to colored latex particles. However, it requires a strong immobilization of MetEEF1A to remove unbound and/or non-specifically bound antigens in previous washing steps.

In general, all methods for detection include intensive washing steps to separate unbound and/or non-specifically bound antigens from the MetEEF1A/antibody complex. Furthermore, the experimental procedure of any detection method is well-known to those skilled in the art.

Another favorite detection method for specific incubation products of the invention is western blotting. Firstly, a gel is mixed and cast, samples previously prepared are loaded onto the gel and fractionated by electrophoresis. The proteins present in the polyacrylamide gel are blotted onto a nitrocellulose membrane to which antibodies may be applied to detect the specific protein of interest, MetEEF1A. Because the blotting process is not 100% efficient, residual MetEEF1A in the gel may be non-selectively stained using Coomassie Blue. Western blotting is simply performed and advantageously when an exact determination of the concentration is dispensable.

There is a distinct number of specific antibodies against EEF1A existing. Antibodies are usually produced in mammal organisms when an immune response is caused by antigens being strange to the organism and having a molecular weight which exceeds 3.000 g/mol. In detail, polyclonal antibodies are known which are directed to the human EEF1A1 antigen. Favorable host species for antibody production comprise goat, rabbit, and mouse. Further polyclonal and monoclonal antibodies can be selected against EEF1A originated form different species and fragments thereof. Popular techniques, such as the hybridoma technology, are well-known to the skilled artisan. The antibodies directed against EEF1A are applied as specific substances in the inventive method.

A signal from the direct or indirect label can be analyzed, for example, using a spectrophotometer to detect color from a chromogenic substrate, using a radiation counter to detect radiation, such as a gamma counter for detection of $^{125}$I, or using a fluorometer to detect fluorescence in the presence of light of a certain wavelength. For detection of enzyme-linked antibodies, a quantitative analysis can be made using a spectrophotometer, such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously.

The antibodies can be immobilized onto a variety of solid supports, such as magnetic or chromatographic matrix particles, the surface of an assay plate {e.g. microtiter wells), pieces of a solid substrate material or membrane {e.g. plastic, nylon, paper) and the like. An assay strip can be prepared by coating the antibody or a plurality of antibodies in an array on a solid support. This strip can then be dipped into the test sample and processed quickly through washes and detection steps to generate a measurable signal, such as a colored spot.

Useful physical formats comprise surfaces having a plurality of discrete, addressable locations for the detection of a plurality of different biomarkers. Such formats include protein microarrays or protein chips. In these embodiments, each discrete surface location may comprise antibodies to immobilize one or more protein markers for detection at each location. Surfaces may alternatively comprise one or more discrete particles (e.g. microparticles or nanoparticles) immobilized at discrete locations of a surface, where the microparticles comprise antibodies to immobilize one or more protein markers for detection.

The analysis can be carried out in a variety of physical formats. For example, the use of microtiter plates or automation could be used to facilitate the processing of large numbers of test samples. Alternatively, single sample formats could be developed to facilitate diagnosis or prognosis in a timely fashion.

Optical images viewed and optionally recorded by a camera or other recording device (e.g. a photodiode and data storage device) are optionally further processed in any of the embodiments herein, e.g. by digitizing the image and storing and analyzing the image on a computer. A variety of commercially available peripheral equipment and software is available for digitizing, storing and analyzing a digitized video or digitized optical image. One conventional system carries light from the specimen field to a cooled charge-coupled device (CCD) camera, in common use in the art. A CCD camera includes an array of picture elements (pixels). The light from the specimen is imaged on the CCD. Particular pixels corresponding to regions of the specimen are sampled to obtain light intensity readings for each position. Multiple pixels are processed in parallel to increase speed. The apparatus and methods of the invention are easily used for viewing any sample, e.g. by fluorescent or dark field microscopic techniques.

In another embodiment of the present invention, analysis of the biomarker can be achieved, for example by high pressure liquid chromatography (HPLC) and/or mass spectrometry, e.g. matrix-assisted laser desorption/ionization mass spectrometry (MALDI-MS), matrix-assisted laser desorption/ionization time-of-flight mass spectrometry (MALDI-TOF/MS), tandem MS, etc., preferably mass spectrometry, more preferably MALDI-TOF/MS or tandem MS. The analysis of the biomarker comprises the determination of the complete protein mass and/or the determination of protein fragments. Preferably, at least the complete mass is determined, which is optionally followed by the determination of fragment masses. Considering MALDI-TOF, the biomarker is adsorbed in a suited matrix showing a high absorption at the excited laser wave length, thereby preventing the generation of fragment ions. The biomarker remains stable by the gentle generation of ions enabling the separation from other cellular components. The detection of time-of-flight mass spectrometers is based on a mass separation principle in high vacuum. To be considered are ionized species starting from the same position at the same time, being accelerated by means of a constant homogeneous electrostatic field. Their velocities are unambiguously related to their mass-to-charge ratio, and times of arrival at a detector directly indicate their masses.

It is still another embodiment of the invention to perform the biomarker determination by sequencing or electrophoresis. Non-limiting examples of sequence analysis include Edman sequencing, capillary array sequencing, thermal cycle sequencing, solid-phase sequencing, sequencing with mass spectrometry, such as MALDI-TOF/MS and sequencing by hybridization, preferably Edman sequencing. Non-limiting examples of electrophoretic analysis include slab gel electrophoresis, such as agarose or polyacrylamide gel electrophoresis, capillary electrophoresis, denaturing gradient gel electrophoresis and isoelectric focusing electrophoresis (IEF), preferably 1D IEF. IEF analysis is especially stained by Coomassie Blue or silver.

Electrochemical processes and probes are also well-established and described in WO 2003/060464 A2, for example, which is incorporated by reference herein.

In a preferred embodiment of the invention, the induction and accumulation of MetEEF1A is detected by IEF along a first dimension followed by at least one method that is selected from the group of western blotting, mass spectrometry and N-terminal sequencing. MetEEF1A bearing the methionine terminal residue is more positively charged at neutral pH in comparison with the constitutive acetylated isoform EEF1A, which allows the two isoforms to be separated by pI. Consequently, the antibody for western blotting does not have to be mono-specific to MetEEF1A, but any specific antibody to EEF1A in general can be applied, i.e. those being reactive to all isoforms of EEF1A or specific to the two isoforms of EEF1A starting either with an acetylated glycine (acGlyEEF1A) or a methionine (MetEEF1A). The prior teaching concerning the single application of the detection methods is valid and applicable without restrictions to combinations thereof.

In another embodiment of the screening method, the detection of MetAP2 inhibition can be additionally refined in step (c). For this purpose, step (c) comprises the further sub-steps of:

(c') correlating an amount of signal or change in signal with a MetEEF1A concentration in the system, and (c") detecting a level of MetAP2 inhibition by comparing the MetEEF1A concentration with another MetEEF1A concentration in a cellular system being not incubated with the compounds and/or in a cellular system being incubated with a standard compound having MetAP2 inhibiting activity.

The cellular system of the invention is incubated with various concentrations of an identified MetAP2 inhibitor. The amount of emitted signal or change in signal observed in the presence of the inhibitor is indicative of the change in activity experienced by the compound. The change in signal is a change in the signal intensity and/or the signal lifetime. It does not matter whether the change in signal results in a decrease or increase of the signal. Even the loss of any signal is regarded as change in signal. The signal amount or change, respectively, can be then related to the concentration of the inhibitor in the sample, i.e. the calibration curve enables the meter-reading of a matching concentration. Preferably, the calibration curve is based on the Lambert-Beer equation if using UV/VIS coloring or luminescence. The concentration of the biomarker is subsequently calculated by considering the molar part of MetEEF1A within the product complex if present. Preferably, the molar ratio of specific substance and MetEEF1A is 1:1, which is present in antibody/MetEEF1A complexes for instance, so that the molar concentration of the incubation products corresponds to the molar concentration of MetEEF1A.

Efficacy of compounds is diagnosed by comparing the concentration of MetEEF1A in the sample with known MetEEF1A concentration levels of either non-treated cells and/or treated cells. It shall be understood that the known concentrations are statistically proven, therefore representing a certain level or range, respectively. Any measured concentration, which differs from the MetEEF1A concentration level of untreated cells, indicates an abnormality of the tested cell sample, whereas a compound cannot be classified as inhibitor at a MetEEF1A concentration that is comparable to the concentration level of untreated cells. It is preferred to measure concentrations, which are higher than the gene product concentration level of untreated cells, for detecting MetAP2 inhibition. Using this method, the inventors demonstrated sensitivity to submicromolar or even nanomolar concentrations. The calibration plot reveals that the method can be applied in a dynamic range that spans over a couple of magnitude.

According to another embodiment to assess the efficacy of compounds, the present screening method is performed such that furthermore in step (c) EEF1A with acetylated N-terminal glycine residue (acGlyEEF1A) is determined, in step (c') an amount of signal or change in signal is correlated with an acGlyEEF1A concentration in the system and optionally a ratio of MetEEF1A to acGlyEEF1A is determined, and in step (c") the acGlyEEF1A concentration and/or the ratio of MetEEF1A to acGlyEEF1A is compared with another acGlyEEF1A concentration and/or another ratio of MetEEF1A to acGlyEEF1A in a cellular system being not incubated with the compounds and/or in a cellular system being incubated with a standard compound having MetAP2 inhibiting activity. The prior teaching concerning the determination, correlation and detection in view of MetEEFF1A is valid and applicable without restrictions to the detection of acGlyEEF1A if expedient.

Among those compounds being revealed to reduce MetAP2 activity, each or some representatives are selected for further analysis. In a preferred embodiment of the present invention, the screening method involves another step (d), which comprises the detection of the specific interaction of compounds with a metAP2 gene or a gene product thereof, or a regulator protein, or a component of a signal transduction pathway comprising said gene or a gene product thereof, provided that the aforementioned interaction results in the decrease or even inhibition of MetAP2 activity. It is preferred to detect the specific binding of compounds to the MetAP2 protein target. Preferably, the compounds showing the greatest discrepancy to the control are chosen. They are analyzed for specificity to exclude another signal transduction, which is not initiated by the binding to the MetAP2 protein target of the invention or associated molecules thereof, and additionally tested for such cross-reactivity in order to prevent adverse reactions or other effects by linked pathways if simultaneous docking to further target structures occurs. Several methods are known in the field of the art for detecting specific and/or mono-specific binding, such as gel shift experiments, Biacore measurements, X-ray structure analysis, competitive binding studies, and the like. In a preferred embodiment of the screening method, the mono-specific binding of substances to the target structures of the invention is detected.

The direction and strength of MetEEF1A expression can also been figured out by the differential protein processing analysis of the biomarker of the invention such that either a distinct up-regulation or down-regulation of activity can be recognized, which forms the basis of compound selection. Although the screening of compounds, which inhibit MetAP2 activity, is preferred in the scope of the present invention, the method can also address the screening of MetAP2 activators. More generally, the invention also relates to a method for screening compounds, which alter MetAP2 activity, comprising the steps of:

(a) providing a cellular system or a sample thereof being capable of expressing MetAP2, wherein the system is selected from the group of single cells, cell cultures, tissues, organs and mammals, (b) incubating at least a portion of the system with compounds to be screened, (c) determining MetEEF1A, (c') correlating an amount of signal or change in signal with a MetEEF1A concentration in the system, (c") detecting the MetAP2 activity by comparing the MetEEF1A concentration with another MetEEF1A concentration in a cellular system being not incubated with the compounds and/or in a cellular system being incubated with a standard compound having MetAP2 activating or MetAP2 inhibiting activity, and optionally (d) detecting the specific interaction of compounds, which alter the MetAP2 activity, with a metAP2 gene, or a regulator protein or a gene product thereof, or a component of a signal transduction pathway comprising said gene or a gene product thereof.

The MetAP2 activation refers to any observable or measurable decrease in the levels of MetEEF1A expression in comparison to a control system. Contrary to that, the MetAP2 inhibition refers to any observable or measurable increase in the levels of MetEEF1A expression in comparison to a control system. The measurement of levels of expression may be carried out using any techniques that are capable of protein biomarkers in a biological sample. Examples of these techniques are discussed above. It is another embodiment of the present invention that in the case of modulating the EEF1A processing, MetEEF1A concentration either under-runs or exceeds at least twice the MetEEF1A concentration in the control system, preferably at least 10 times, more preferably at least 25 times, most preferably at least 40 times. In a highly preferred embodiment of the invention, MetAP2 activation results in the complete conversion of MetEEF1A into acGlyEEF1A (i.e. lack of MetEEF1A), whereas MetAP2 inhibition results in the complete preservation of MetEEF1A (i.e. exclusive appearance of MetEEF1A).

The prior teaching of the present specification concerning the method for screening MetAP2 inhibitors is considered as valid and applicable without restrictions to the method for screening MetAP2 modulators if expedient. Particularly, the prior and ongoing teaching concerning MetAP2 inhibitors is valid and applicable without restrictions to MetAP2 activators if expedient; in doing so it shall be understood for the skilled artisan that certain effects of activating and inhibiting compounds are inherently diametrical.

The method of the invention is preferably applied for screening compounds that provide anti-proliferative activity. Herein, a proliferative cell culture is applied, such as a small cell lung carcinoma, a non-small cell lung carcinoma, an osteosarcoma, a human breast carcinoma or a contact inhibited mouse fibroblast cell line in particular. Consequently, it is particularly preferred to screen compounds with angiogenic and/or anti-tumor activity. Such activities are associated with physiological and/or pathological conditions, which are caused, mediated and/or propagated by MetAP2 activity. The MetAP2 inhibitors are highly useful as cytotoxic agents for treating proliferative diseases, preferably cancer including tumors and metastasis. MetAP2 inhibitors are particularly suitable for inhibiting the growth of various lymphomas, sarcomas, carcinomas and myelomas. In addition, MetAP2 inhibitors are suitable for treating angiogenesis-dependent diseases, e.g. various ocular neovascular diseases.

The invention also teaches an embodiment of the method for screening therapeutic compounds for an anti-proliferative indication, wherein in step (a) a mammal is provided, in step (b) the compound to be screened are administered to the mammal, and in step (c) a therapeutic effect is detected by determining MetEEF1A in a biological sample withdrawn from the mammal. It shall be understood that the expression "therapeutic compounds for an anti-proliferative indication" refers to the use of suited compounds in the treatment of clinical pictures, which are characterized by excessive, uncontrolled and accelerated cell growth, division and propagation, and hence, the compounds are therapeutic in the anti-proliferative application.

The mammal of step (a) is preferably a non-human organism, more preferably a laboratory animal, most preferably species such as mice or rats that may be genetically modified. The mammal suffers from any proliferative clinical picture that is associated with a minor or even absent MetEEF1A level. This expression level of the biomarker MetEEF1A on protein basis is measured in a biopsy sample, such as a tissue sample from tumor tissue or plasma of said mammalian patient, and set as base-line.

In step (b), it is possible to contact mice or rats, for example, with the compound candidates by injection, infusion, oral or rectal intake. It is preferred to incubate a single compound within a distinct portion of the non-human organisms. Step b) can also be performed in-vitro by exposing ex-vivo a sample, such as a tissue sample from tumor or plasma of the mammalian patient to said anti-MetAP2 drug. A human patient is preferred if performing step (b) in-vitro.

In step (c), the MetEEF1A expression level is measured again in an identical manner to step a), and differences in the expression levels measured in step a) and c) are calculated. Any difference is inherently based on a change to the initial base-line, thereby confirming an interaction of a defined screening compound with MetAP2. The desired increase in levels of MetEEF1A expression indicates a successful MetAP2 inhibition, which is to be correlated to the therapeutic effect. Such a relationship can be established by monitoring the chronological sequence of the effect against a single or multiple dose of the defined screening compound by using the treated mammal only. The effect is determined either by means of qualitative parameters, e.g. decreasing severity of symptoms, or quantitative parameters, e.g. reduced rate of cell growth rate, diminished tumor size, etc. An increase in the expression level of the biomarkers MetEEF1A obtained in step (c) compared to step (a) indicates an increased likelihood that said mammal responds therapeutically to the treatment with said screening compound. This increase may approach a threshold under the proviso that the comparison is performed with a healthy control mammal (i.e. lacking any proliferative abnormality), which inherently exhibits a down-regulated MetAP2 activity. Accordingly, the determination of step (c) is favorably performed in comparison with another mammal showing non-proliferative and/or proliferative effects. The comparative mammal is not exposed to compounds to be screened, but treated in an identical manner to measure MetEEF1A levels. Step (c) preferably comprises the further sub-steps of:

(c') correlating an amount of signal or change in signal with a MetEEF1A concentration in the system, and (c") detecting a level of anti-proliferative activity by comparing the MetEEF1A concentration with another MetEEF1A concentration in a system of non-proliferative and/or proliferative cells.

It is additionally preferred within this embodiment that at least two subjects of a non-human organism suffering of a proliferative disorder are provided as sample, a subset of them the compounds are administered, and the protein processing pattern is correlated to the symptoms of the disorder in subjects to which compounds have been administered and subjects to which no compounds have been administered. It goes without saying that the basic principles of the general screening method are valid and applicable without restrictions to any special embodiment hereunder, if expedient.

With the therapeutic effect, the qualitative level is incorporated into step (c). A "therapeutically relevant effect" relieves to some extent one or more symptoms of a disease or returns to normality, either partially or completely, one or more physiological or biochemical parameters associated with or causative of the disease or pathological conditions. In addition, the expression "therapeutically effective amount" denotes an amount which, compared with a corresponding subject who has not received this amount, has the following consequence: improved treatment, healing, prevention or elimination of a disease, syndrome, condition, complaint, disorder or side-effects or also the reduction in the advance of a disease, complaint or disorder. The expression "therapeutically effective amount" also encompasses the amounts which are effective for increasing normal physiological function. Testing of several compounds makes the selection of that compound possible that is best suited for the treatment of the mammal subject. The in-vivo dose rate of the chosen compound is advantageously pre-adjusted to the proliferation of the specific cells with regard to their in-vitro data. Therefore, the therapeutic efficacy is remarkably enhanced.

A compound identified by the screening method is another object of the invention. The prior teaching of the present specification concerning the screening method is valid and applicable without restrictions to the compound itself if expedient.

The identification of compounds that alter the MetAP2 activity, preferably inhibit the MetAP2 activity, which is associated with a given disorder or condition, can lead to the development of pharmaceuticals that can be administered to a patient at therapeutically effective doses to prevent, treat or control such disorder or condition. Hence, the invention furthermore relates to a medicament comprising at least one compound according to the invention, and optionally excipients and/or adjuvants. In the meaning of the invention, an "adjuvant" denotes every substance that enables, intensifies or modifies a specific response against the active ingredient of the invention if administered simultaneously, contemporarily or sequentially. Known adjuvants for injection solutions are, for example, aluminum compositions, such as aluminum hydroxide or aluminum phosphate, saponins, such as QS21, muramyldipeptide or muramyltripeptide, proteins, such as gamma-interferon or TNF, M59, squalen or polyols. Consequently, the invention also relates to a pharmaceutical composition comprising as active ingredient an effective amount of at least one compound as screened according to the invention and/or physiologically acceptable salts thereof together with pharmaceutically tolerable adjuvants.

A "medicament", "drug", "pharmaceutical composition" or "pharmaceutical formulation" in the meaning of the invention is any agent in the field of medicine, which comprises one or more MetAP2 inhibitors of the invention or preparations thereof and can be used in prophylaxis, therapy, follow-up or aftercare of patients who suffer from diseases, which are associated with MetAP2 signaling, in such a way that a pathogenic modification of their overall condition or of the condition of particular regions of the organism could establish at least temporarily.

Furthermore, the active ingredient may be administered alone or in combination with other treatments. A synergistic effect may be achieved by using more than one compound in the pharmaceutical composition, i.e. the MetA2 inhibitor of the invention is combined with at least another agent as active ingredient. The active ingredients can be used either simultaneously or sequentially.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

The pharmaceutical composition of the invention is produced in a known way using common solid or liquid carriers, diluents and/or additives and usual adjuvants for pharmaceutical engineering and with an appropriate dosage. The amount of excipient material that is combined with the active ingredient to produce a single dosage form varies depending upon the host treated and the particular mode of administration. Suitable excipients include organic or inorganic substances that are suitable for the different routes of administration, such as enteral (e.g. oral), parenteral or topical application, and which do not react with compounds of the invention or salts thereof. Examples of suitable excipients are water, vegetable oils, benzyl alcohols, alkylene glycols, polyethylene glycols, glycerol triacetate, gelatin, carbohydrates, such as lactose or starch, magnesium stearate, talc, and petroleum jelly.

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavor, preservative, dispersant and dye may likewise be present.

Capsules are produced by preparing a powder mixture as described above and filling shaped gelatin shells therewith. Glidants and lubricants, e.g. highly disperse silicic acid, talc, magnesium stearate, calcium stearate or polyethylene glycol in solid form, can be added to the powder mixture before the filling operation. A disintegrant or solubiliser, such as agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatin, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatin or polyvinylpyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavor, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavor additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds according to the invention and salts, solvates and physiologically functional derivatives thereof can be administered in the form of liposome delivery systems, such as small unilamellar vesicles, large unilamellar vesicles and multilamellar vesicles. Liposomes can be formed from various phospholipids, such as cholesterol, stearylamine or phosphatidylcholines.

The active ingredient according to the invention can also be fused or complexed with another molecule that promotes the directed transport to the destination, the incorporation and/or distribution within the target cells.

The compounds according to the invention and the salts, solvates and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamido-phenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils. For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base. Pharmaceutical formulations adapted for topical application to the eye include eye drops, in which the active ingredient is dissolved or suspended in a suitable carrier, in particular an aqueous solvent. Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurized dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilized) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavors.

In a preferred embodiment of the present invention, the pharmaceutical composition is orally or parenterally administered, more preferably orally. In particular, the active ingredient is provided in a water-soluble form, such as a pharmaceutically acceptable salt, which is meant to include both acid and base addition salts. Furthermore, the compounds of the invention and salts thereof may be lyophilized and the resulting lyophilizates used, for example, to produce preparations for injection. The preparations indicated may be sterilized and/or may comprise auxiliaries, such as carrier proteins (e.g. serum albumin), lubricants, preservatives, stabilizers, fillers, chelating agents, antioxidants, solvents, bonding agents, suspending agents, wetting agents, emulsifiers, salts (for influencing the osmotic pressure), buffer substances, colorants, flavorings and one or more further active substances, for example one or more vitamins. Additives are well known in the art, and they are used in a variety of formulations.

Pharmaceutical formulations can be administered in the form of dosage units which comprise a predetermined amount of active ingredient per dosage unit. The concentration of the prophylactically or therapeutically active ingredient in the formulation may vary from about 0.1 to 100 wt %. Preferably, the compound of formula (I) or the pharmaceutically acceptable salts thereof are administered in doses of approximately 0.5 to 1000 mg, more preferably between 1 and 700 mg, most preferably 5 and 100 mg per dose unit. Generally, such a dose range is appropriate for total daily incorporation. In other terms, the daily dose is preferably between approximately 0.02 and 100 mg/kg of body weight. The specific dose for each patient depends, however, on a wide variety of factors (e.g. depending on the condition treated, the method of administration and the age, weight and condition of the patient). Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

The invention also relates to a method for monitoring physiological and/or pathological conditions, which are caused, mediated and/or propagated by MetAP2 activity, wherein an effective amount of at least one compound or a physiologically acceptable salt thereof is administered to a mammal in need of such treatment and MetEEF1A is determined in a biological sample withdrawn from the mammal. An increase in the expression level of said biomarker over the period of monitoring indicates a decreased MetAP2 activity, which is associated with an increased likelihood that said mammal responds to the treatment with said compound. The compound is preferably obtained by the screening method of the invention as set forth above. Thus, the prior teaching of the present specification concerning the screening method is valid and applicable without restrictions to method of monitoring if expedient.

The identification of EEF1A described above provides a powerful tool for assessing the progression of a state, condition or treatment. The present invention can be used as a clinical marker to monitor efficacy of a MetAP2 inhibitor compound on each patient individually. Specifically, EEF1A can be identified in a patient prior to an event, such as menopause, surgery, the onset of a therapeutic regime, or the completion of a therapeutic regime, to provide a base line result. This base-line can then be compared with the result obtained using identical methods either during or after such event. This information can be used for both diagnostic and prognostic purposes. The information about the clinical marker can be additionally used to optimize the dosage and the regimen of an active compound by monitoring the induction and accumulation of MetEEF1A in the subject's biological sample. Furthermore, the method of the present invention can be used to find a therapeutically effective compound and/or a therapeutically effective amount or regimen for the selected compound, thereby individually selecting and optimizing a therapy for a patient.

Accordingly, the inventive method of monitoring can be employed in human and veterinary medicine. The mammal is preferably a laboratory animal and/or a non-human organism. Herein, the compounds can be administered before or following an onset of disease once or several times acting as therapy. The terms "effective amount" or "effective dose" or "dose" are interchangeably used herein and denote an amount of the pharmaceutical compound having a prophylactically or therapeutically relevant effect on a disease or pathological conditions, i.e. which causes in a tissue, system, animal or human a biological or medical response which is sought or desired, for example, by a researcher or physician.

The aforementioned medical products of the inventive use are particularly used for the therapeutic treatment. Monitoring is considered as a kind of treatment, wherein the compounds are preferably administered in distinct intervals, e.g. in order to booster the response and eradicate the pathogens and/or symptoms of the MetAP2-related disease completely. Either the identical compound or different compounds can be applied. The medicament can also be used to reduce the likelihood of developing a disease or even prevent the initiation of diseases associated with MetAP2 activity in advance or to treat the arising and continuing symptoms. In the meaning of the invention, prophylactic treatment is advisable if the subject possesses any preconditions for the aforementioned physiological or pathological conditions, such as a familial disposition, a genetic defect, or a previously passed disease.

The diseases as concerned by the invention are cancerous diseases, which are selected from the group of cancerous diseases of the ear-nose-throat region, the lungs, mediastinum, gastrointestinal tract, urogenital system, gynecological system, breast, endocrine system, skin and bone, furthermore soft-tissue sarcomas, mesotheliomas, melanomas, neoplasms of the central nervous system, cancerous diseases during infancy, lymphomas, leukemias, paraneoplastic syndromes, metastases with unknown primary tumor (CUP syndrome), peritoneal carcinomatoses, immunosuppression-related malignancies and/or tumor metastases. More specifically, the tumors may be designated as the following type of cancer: adenocarcinoma of breast, prostate and colon; all forms of lung cancer starting in the bronchial tube; bone marrow cancer, melanoma, hepatoma, neuroblastoma, papilloma; apudoma, choristoma, branchioma, malignant carcinoid syndrome, carcinoid heart disease, carcinoma (e.g. Walker carcinoma, basal cell carcinoma, squamobasal carcinoma, Brown-Pearce carcinoma, ductal carcinoma, Ehrlich tumor, in-situ carcinoma, cancer-2 carcinoma, Merkel cell carcinoma, mucous cancer, non-parvicellular bronchial carcinoma, oat-cell carcinoma, papillary carcinoma, scirrhus carcinoma, bronchio-alveolar carcinoma, bronchial carcinoma, squamous cell carcinoma and transitional cell carcinoma), histiocytic functional disorder, leukemia (e.g. in connection with B cell leukemia, mixed-cell leukemia, null cell leukemia, T cell leukemia, chronic T cell leukemia, HTLV-II-associated leukemia, acute lymphocytic leukemia, chronic lymphocytic leukemia, mast cell leukemia, and myeloid leukemia), malignant histiocytosis, Hodgkin disease, non-Hodgkin lymphoma, solitary plasma cell tumor; reticuloendotheliosis, chondroblastoma; chondroma, chondrosarcoma; fibroma; fibrosarcoma; giant cell tumors, histiocytoma, lipoma, liposarcoma, leukosarcoma, mesothelioma, myxoma, myxosarcoma, osteoma, osteosarcoma, Ewing sarcoma, synovioma, adenofibroma, adenolymphoma, carcinosarcoma, chordoma, craniopharyngioma, dysgerminoma, hamartoma, mesenchymoma, mesonephroma, myosarcoma, ameloblastoma, cementoma; odontoma, teratoma; thymoma, chorioblastoma, adenocarcinoma, adenoma, cholangioma, cholesteatoma, cylindroma, cystadenocarcinoma, cystadenoma, granulosa cell tumor, gynadroblastoma, hidradenoma, islet-cell tumor, Leydig cell tumor, papilloma, Sertoli cell tumor, theca cell tumor, leiomyoma, leiomyosarcoma, myoblastoma, myoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, non-chromaffin paraganglioma, angiokeratoma, angiolymphoid hyperplasia with eosinophilia, sclerotizing angioma, angiomatosis, glomangioma, hemangioendothelioma, hemangioma, hemangiopericytoma, hemangiosarcoma, lymphangioma, lymphangiomyoma, lymphangiosarcoma, pinealoma, cystosarcoma phylloides, hemangiosarcoma, lymphangiosarcoma, myxosarcoma, ovarian carcinoma, sarcoma (e.g. Ewing sarcoma, experimentally, Kaposi sarcoma and mast cell sarcoma), neoplasms (e.g. bone neoplasms, breast neoplasms, neoplasms of the digestive system, colorectal neoplasms, liver neoplasms, pancreas neoplasms, hypophysis neoplasms, testicle neoplasms, orbital neoplasms, neoplasms of the head and neck, the central nervous system, neoplasms of the hearing organ, pelvis, respiratory tract and urogenital tract), neurofibromatosis and cervical squamous cell dysplasia.

The tumor is preferably selected from the group of tumors of the squamous epithelium, the bladder, the stomach, the kidneys, the head, the neck, the oesophagus, the cervix, the thyroid, the intestine, the liver, the brain, the prostate, the urogenital tract, the lymphatic system, the stomach, the larynx and/or the lung.

The tumor is furthermore preferably selected from the group of lung adenocarcinoma, small-cell lung carcinomas, pancreatic cancer, glioblastomas, colon carcinoma and breast carcinoma. In addition, preference is given to the treatment and/or monitoring of a tumor of the blood and immune system, more preferably for the treatment and/or monitoring of a tumor selected from the group of acute myeloid leukemia, chronic myeloid leukemia, acute lymphatic leukemia and/or chronic lymphatic leukemia. Such tumors can also be designated as cancers in the meaning of the invention.

In another embodiment of the present invention, oral tongue squamous cell carcinoma, head squamous cell carcinoma, neck squamous cell carcinoma, pancreas cancer and breast cancer are disclaimed from the subject-matter which is sought by the method for monitoring.

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. The expressions "pharmaceutically acceptable salt" and "physiologically acceptable salt", which are used interchangeable herein, in the present connection are taken to mean an active ingredient which comprises a compound according to the invention in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The invention also relates to a method for determining MetAP2 activity comprising the steps of:
(a) providing a cellular system or a sample thereof being capable of expressing MetAP2, wherein the system is selected from the group of single cells, cell cultures, tissues, organs and mammals,
(b) incubating at least a portion of the system with compounds to be screened, and
(c) determining the MetAP2 activity by determining MetEEF1A and correlating an amount of signal or change in signal with a MetEEF1A concentration in the system, wherein the MetAP2 activity and the MetEEF1A concentration are inversely proportional.

By means of the inventive method, any partial activity between complete inhibition or maximal activity can be set or even the aforementioned thresholds can be achieved. The inverse proportionality can follow either a linear or a non-linear function. Moreover, the prior teaching concerning the methods for screening compounds as well as monitoring physiological and/or pathological conditions is valid and applicable without restrictions to the method for determining MetAP2 activity.

Moreover, the invention relates to an in-vitro method for predicting the likelihood that a patient suffering from a tumor, who is a candidate for treatment with an anti-MetAP2 drug, will respond to the treatment with said drug, comprising the determination of the expression level of a prognostic gene expression product, which is MetEEF1A, in a tissue sample obtained from said patient, wherein a higher expression of the gene product indicates that the patient is likely to respond to said treatment compared to a reference value. The treatment with said anti-MetAP2 drug can be a first-line mono-therapy and the selected gene expression product is the expressed protein MetEEF1A. Alternatively, the treatment with said anti-MetAP2 drug is a combination therapy with a chemotherapeutic agent after the patient has developed a chemo-refractory tumor, and the selected gene expression product is the expressed protein MetEEF1A. The reference value is defined by one or more of a specific functional or clinical property, and/or a specific, genetic or protein expression profile obtained from a reference patient or reference patient group. Said reference patient or patient group that does not express or express less gene product compared to the candidate patient. The reference value is an expression threshold value which is individually constituted or defined by specific clinical response parameters to be determined or by specific pre-treatment or treatment conditions. Suitable clinical response parameters are the progression free survival time (PFS), overall survival time (OS), partial response (PR), stable response (SR), progressive disease (PD) or combinations thereof. Tissue samples are taken from the patient before treatment with said anti-MetAP2 drug and additionally on treatment with said anti-MetAP2 drug. The expression levels of the gene expression product obtained on treatment are compared with the values obtained before starting treatment of said patient. The patient sample derives from tumor tissue or plasma, for example.

Another in-vitro method for predicting the likelihood that a patient suffering from a proliferative-driven disorder or condition, particularly cancer, will respond therapeutically to the treatment with an anti-MetAP2 drug comprises the steps of (a) measuring in a biopsy tissue sample from tumor tissue or plasma of said patient the expression level of MetEEF1A biomarker on protein basis, (b) exposing ex-vivo a tissue sample from tumor or plasma of said patient to said anti-MetAP2 drug, and (c) measuring in said exposed tissue sample of step (b) the expression level of said biomarker specified in step (a) along with calculating the differences in expression levels measured in steps (b) and (c), wherein an increase in the expression level of said biomarker obtained in this step (c) compared to step (a) indicates an increased likelihood that said patient responds therapeutically to the treatment with said anti-MetAP2 drug.

Object of the invention is also the use of EEF1A1 comprising the amino acid sequence of SEQ ID NO: 1 and/or EEF1A2 comprising the amino acid sequence of SEQ ID NO: 2 (cf. FIG. 11), or variants, mutants, parts of the amino acid sequence or at least 85 homologous sequences having the same function, or a nucleic acid encoding EEF1A1 and/or a nucleic acid sequence encoding EEF1A2, as biomarker for a reduction of MetAP2 activity. Another object of the invention relates to the use of EEF1A as biomarker for cell proliferation under the proviso that oral tongue squamous cell carcinoma, head squamous cell carcinoma, neck squamous cell carcinoma, pancreas cancer and breast cancer are disclaimed. It is still another object of the invention to use EEF1A as biomarker for a reduction of likelihood of developing a tumor and/or progressive tumor growth under the proviso that breast cancer is disclaimed. A preferred use concerns the application of EEF1A as angiogenic and/or tumor inhibition.

The biomarker can be used for monitoring, determining and/or predicting the reduction of MetAP2 activity, the status of cell proliferation and/or the reduction of likelihood of developing a tumor and/or a progressive tumor growth. The different uses can be subsumed under the general term "assessing". It goes without saying that data are monitored over a specific period, while data are determined at a particular time. Both the period and the time can be easily designed by the skilled artisan depending on the experimental trials conducted. Moreover, EEF1A can be used as biomarker for predicting in-vitro the pharmaceutical efficacy and/or clinical response of a mammal suffering from cancer to a MetAP2-inhibiting drug, which is intended to be administered and/or is administered in cancer treatment. The underlying treatment is particularly a first-line treatment, and the inhibitory drug with which the mammalian patient is to be treated, is administered in mono-therapy. In an alternative embodiment of the underlying treatment, said drug is combined with a chemotherapeutic agent, and said patient has developed chemo-refractory cancer.

Another preferred use concerns that of MetEEF1A1 and/or MetEEF1A2 as biomarker. The prior teaching of the present specification concerning the screening method is valid and applicable without restrictions to any of said uses if expedient.

Further, the invention may be practiced as a kit comprising substances specifically interacting with EEF1A, preferably MetEEF1A, particularly in order to perform the inventive method for detecting and/or characterizing MetAP2 activity. The kit of the invention may include an article that comprises written instructions or directs the user to written instructions for how to practice the method of the invention. In an embodiment, the kit further comprises a reporter moiety or a reporter apparatus. Additionally, the kit may comprise an extracting reagent for isolating the biomarker. The prior teaching of the present specification concerning the screening method is considered as valid and applicable without restrictions to the kit if expedient.

In the scope of the present invention, a method for screening MetAP2 inhibitors or modulators by applying the unique biomarker EEF1A is provided for the first time. The present invention teaches the induction and accumulation of MetEEF1A in cells, whose enzymatic MetAP2 activity is interrupted. EEF1A as a biomarker for MetAP2 inhibitors has several advantages. It is an abundant cellular protein so it can be easily detected in tumor samples. The N-terminal status of EEF1A reflects the MetAP2 enzyme activity over a period, thus truly representing the consequence of MetAP2 inhibition and better correlating with efficacy of the testing compound. In addition, the MetEEF1A readout is on MetAP2-specific substrate, but not MetAP2 itself, so it can be used for all types of MetAP2 inhibitors. The substrate is processed by MetAP2, but not by MetAP1, which makes it possible to prove that an anti-angiogenic and anti-proliferative activity is specifically due to inhibition of the proteolytic activity of MetAP2.

Inhibition of methionine processing by MetAP2 blocks tumor cell growth in-vitro. MetAP2 inhibitors even induce MetEEF1A in a dose-dependent fashion similar to that observed for their antiproliferative activity. The robust marker has the potential to monitor MetAP2 inhibition not only in cells but also in animals and human subjects treated with MetAP2 inhibitors. Induction of MetEEF1A also correlated with the in-vivo anti-angiogenic and anti-tumor activity. EEF1A N-terminal status is an outstanding biomarker for cellular MetAP2 inhibition in-vitro and in-vivo. EEF1A processing is of benefit to monitor MetAP2 inhibition in preclinical and clinical testing.

The analysis of the differential processed EEF1A isoform is very suitable for large-scale screening tests. The novel marker allows the identification of novel MetAP2 inhibitors. Compounds can be identified and evaluated with a specific cellular mechanism of action and additionally, their potential to exert anti-angiogenic and/or anti-proliferative effects can be favorably proved. The characterization of EEF1A, particularly MetEEF1A, critically involved in substrate recognition by MetAP2 results in the provision of pharmaceutical compositions for the diagnosis, prophylactic or therapeutic treatment and/or monitoring of conditions, which are caused, mediated and/or propagated by MetAP2 activity. Their use is a promising, novel approach for a broad spectrum of therapies causing a direct and immediate reduction of symptoms that are clearly connected with MetAP2-dependent diseases. The compounds are of special benefit as anti-cancer agents in mammals.

Hence, in in-vitro screening and monitoring such physiological or pathological conditions, EEF1A is qualified as biomarker for detecting and characterizing MetAP2 activity. The detection method as well as arising monitoring method of the invention can be performed in a simple and fast manner. In addition, the appropriate kit is cost-efficiently produced. Targeting EEF1A isoforms is highly specific for the MetAP2 activity and driven medical disorders therefrom. All detecting substances are characterized by a high affinity, specificity and stability; low manufacturing costs and convenient handling. These features form the basis for a reproducible action, wherein the lack of cross-reactivity is included, and for a reliable and safe interaction with their matching target structures.

All the references cited herein are incorporated by reference in the disclosure of the invention hereby.

It is to be understood that this invention is not limited to the particular methods, specific substances, uses and kits described herein, as such matter may, of course, vary. It is also to be understood that the terminology used herein is for the purpose of describing particular embodiments only and is not intended to limit the scope of the present invention, which is only defined by the appended claims. As used herein, including the appended claims, singular forms of words such as "a," "an," and "the" include their corresponding plural referents unless the context clearly dictates otherwise. Thus, e.g., reference to "a substance" includes a single or several different substances, and reference to "a method" includes reference to equivalent steps and methods known to a person of ordinary skill in the art, and so forth. Unless otherwise defined, all technical and scientific terms used herein have the same meaning as commonly understood by a person of ordinary skill in the art to which this invention belongs.

Although methods and materials similar or equivalent to those described herein can be used in the practice or testing of the present invention, suitable examples are described below. The following examples are provided by way of illustration and not by way of limitation. Within the examples, standard reagents and buffers that are free from contaminating activities (whenever practical) are used. The examples are particularly to be interpreted such that they are not limited to the explicitly demonstrated combinations of features, but the exemplified features may be unrestrictedly combined again if the technical problem of the invention is solved.

Cell Culture and Treatment with MetAP2 Inhibitors

Mouse brain endothelioma cells (bEND3, ECACC Nr.9609129) were cultured at 37° C. and 10% $CO_2$ in D-MEM (Invitrogen, #41965) supplemented with 10% (v/v) heat-inactivated fetal bovine serum (Pan Biotech, #3302), 1 mM sodium pyruvate (Invitrogen, #11360) and 1× Nonessential Amino Acid Solution (Sigma, M7145). Human colon carcinoma cells (HCT116, ATCC CCL 225) were cultured at 37° C. and 10% $CO_2$ in MEM alpha (Invitrogen, #22571)

supplemented with 10% (v/v) heat-inactivated fetal bovine serum (Pan Biotech, #3302), 2 mM glutamine (Invitrogen, #25030) and 1 mM sodium pyruvate (Invitrogen, #11360). Human umbilical vein endothelial cells (HUVEC, Promo-Cell, C-12200) are cultivated at 37° C. and 5% $CO_2$ in endothelial cell growth medium (PromoCell, C-22020) with supplement mix (PromoCell, C-39215). Human fibrosarcoma cells (HT1080, ATCC CCL-121) were cultured at 37° C. and 10% $CO_2$ in D-MEM (Invitrogen, #41965) supplemented with 10% (v/v) heat-inactivated fetal bovine serum (Pan Biotech, #3302). Cells were detached from cell culture flasks with trypsin/EDTA (Invitrogen, #15400), counted using a Thoma chamber (VWR, #631-1117) plated in tissue culture dishes (VWR, #391-2002, #391-2003) in fresh medium (cell density: HT1080, bEND3: 0.5 to $1*10^6$ cells in 30 ml medium per 15 cm dish, HCT116: $1*10^6$ cells in 10 ml medium per 10 cm dish). Cells were cultured overnight and treated with vehicle control (0.5% DMSO; Merck, #1.02931) or specific methionine aminopeptidase 2 inhibitors (Fumagillin: Sigma, F-6771; TNP-470; Abbott Inhibitor A-832234: Sheppard et al. (2005) $96^{th}$ AACR Meeting, Abstract #2531) for different times (2 hrs, 6 hrs, 24 hrs, 48 hrs) at indicated concentrations. The medium was collected in falcon tubes and the attached cells were washed twice with Dulbecco's phosphate-buffered saline solution (Invitrogen, #14190). The D-PBS wash was combined with the medium. Attached cells were incubated for 20 minutes with 5 ml versene (Invitrogen, 15040), scraped off the plate, and combined with the medium/wash solution. Cells were centrifuged for 4 minutes at 300*g at room temperature, re-suspended in 0.5 ml D-PBS (Invitrogen, #14190), and counted in a Thoma chamber. The cells were centrifuged again and the supernatant was removed. Subsequently, cells were re-suspended in IEF-lysis buffer (7 M Urea, 2M thiourea, 4% CHAPS, 1% DTT, 1% Pharmalyte pH 3-10 (GE Healthcare) at a density of $2*10^7$ cells per ml and incubated for 30 min with gentle agitation. The lysates were centrifuged for 5 min at 10.000*g, supernatants were collected in fresh eppendorf micro test tubes and finally frozen at −70° C.

IEF Separation

Cellular extracts were electrophoretically separated for detailed analysis. Isoelectric focusing electrophoresis was performed in a gradient range of pH 7-9. The IEF gels (Clean-Gel IEF ultra ETC1001-52 from ETC, Germany) were rehydrated in 7 M urea, 2 M thiourea, 1% DTE, 4% CHAPS, 3%, Servalyte 7-9 for 120 min, and assembled on a Multiphor II electrophoresis unit (GE Healthcare). Samples (5 µl) were applied close to the anode and run with anode buffer (6 M glycine) and cathode fluid 10 (Serva, Germany). After pre-focusing of the gel (700 V, 30 min) sample entry was achieved at 20° C. at 500 V for 30 min. Separation was performed at 2000 V for 210 min, followed by band sharpening at 2500 V for 10 min. After removal the gel was equilibrated in transfer buffer (50 mM Tris-HCl pH 7.5, 4 M guanidinium chloride, 1 mg/ml DTT) for a diffusion blot onto PVDF membrane and run overnight. Subsequently, the membrane was stained either with Coomassie Blue or immunostained with rabbit PcAb anti-human EEF1A1 (Proteintech Group, USA; 11402-1-AP) for 3 h and detected with ECL-Plus reagent (GE Healthcare).

N-Terminal Protein Sequencing

Amino terminal sequence determination was achieved for the various cell extracts after IEF separation, blotting into PVDF membrane and Coomassie Blue staining. Single Coomassie bands were excised and applied onto a Procise 491 protein sequenator (Applied Biosystems, USA) and run according to standard protocol.

Enzymatic Digest and Mass Analysis

Coomassie Blue stained acrylamide gel bands were excised after IEF separation, washed twice with 50% acetonitrile and rinsed with pure acetonitrile. In gel digest was performed by adding 0.1 µg trypsin dissolved in 10 µl ammonium bicarbonate pH 7.4 to the gel band. Incubation was achieved at 37° C. overnight. Aliquots of the digest mix were applied onto a target plate of a MALDI-TOF MS (Ultraflex, Bruker, Germany) and α-cyano-4-hydroxycinnamic acid was added as a matrix. Mass analysis was performed and peptide fragments were detected applying standard protocols. The achieved peptide mass lists were searched against the SwissProt database using the Mascot search algorithm (Matrix Science, UK) to identify the protein. Furthermore, distinct peptides from a mass map were used for subsequent MS-fragmentation studies in order to determine the primary sequence of those individual peptides and for unambiguous protein annotation.

Table 1 contains explanatory information for FIG. 10. Compounds were incubated with bEND3 cells for 48 h at the indicated concentrations, lysed and electrophoretic mobility shift of EEF1A1 was assessed in an IEF gel. The compounds used were characterized as inhibitors of MetAP2 and inhibitors of HUVEC cell proliferation with the indicated potencies (IC50). Inhibition of MetAP2 was measured via cleavage of the tripeptide Met-Ala-Ser and subsequent detection of cleaved methionine using an enzyme-coupling reaction composed of L-amino oxidase and peroxidase (Wang et al. (2003) Biochemistry 42(17): 5035-5042). Inhibition of HUVEC cell proliferation by the indicated compounds was measured using a colorimetric BrdU-Elisa from Roche (Switzerland; Catalogue number: 11 647 229 001). In this case the compounds were incubated in serial dilutions with the HUVEC endothelial cells for 72 h and subsequently processed for BrdU detection.

FIG. 1 shows the treatment-related pattern of cellular extracts from different endothelial and cancer cells after IEF separation with a new band observed after applying MetAP2-inhibitors (lane 1, 5, 9: IEF marker proteins; lane 2, 6, 12: 100 nM TNP470; lane 3, 7: 1 µM 2-[2-((Z)-3-Diethylamino-propenyl)-4-fluoro-benzenesulfonylamino]-5,6,7,8-tetrahydro-naphthalene-1-carboxylic acid, which is identical to A-832234; lane 4, 8, 11: 0.5% DMSO).

Figure 4:
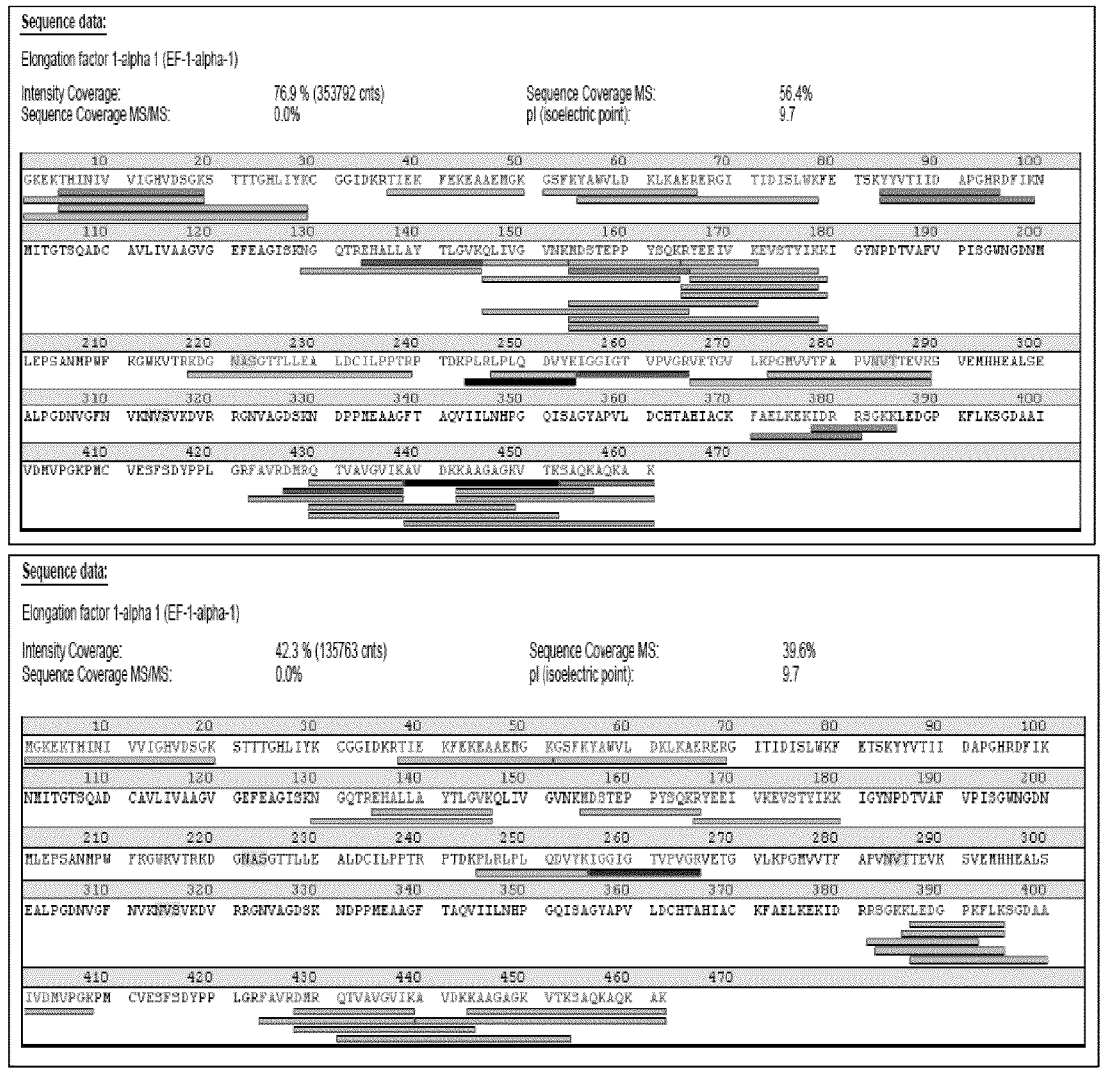

FIG. 4 shows the protein identification after in-gel digestion of Band 1 and Band 2 (cf. FIG. 2) and mass map and database annotation. FIG. 4 discloses residues 2-462 of SEQ ID NO: 1 and SEQ ID NO: 1, respectively.

Figure 5:
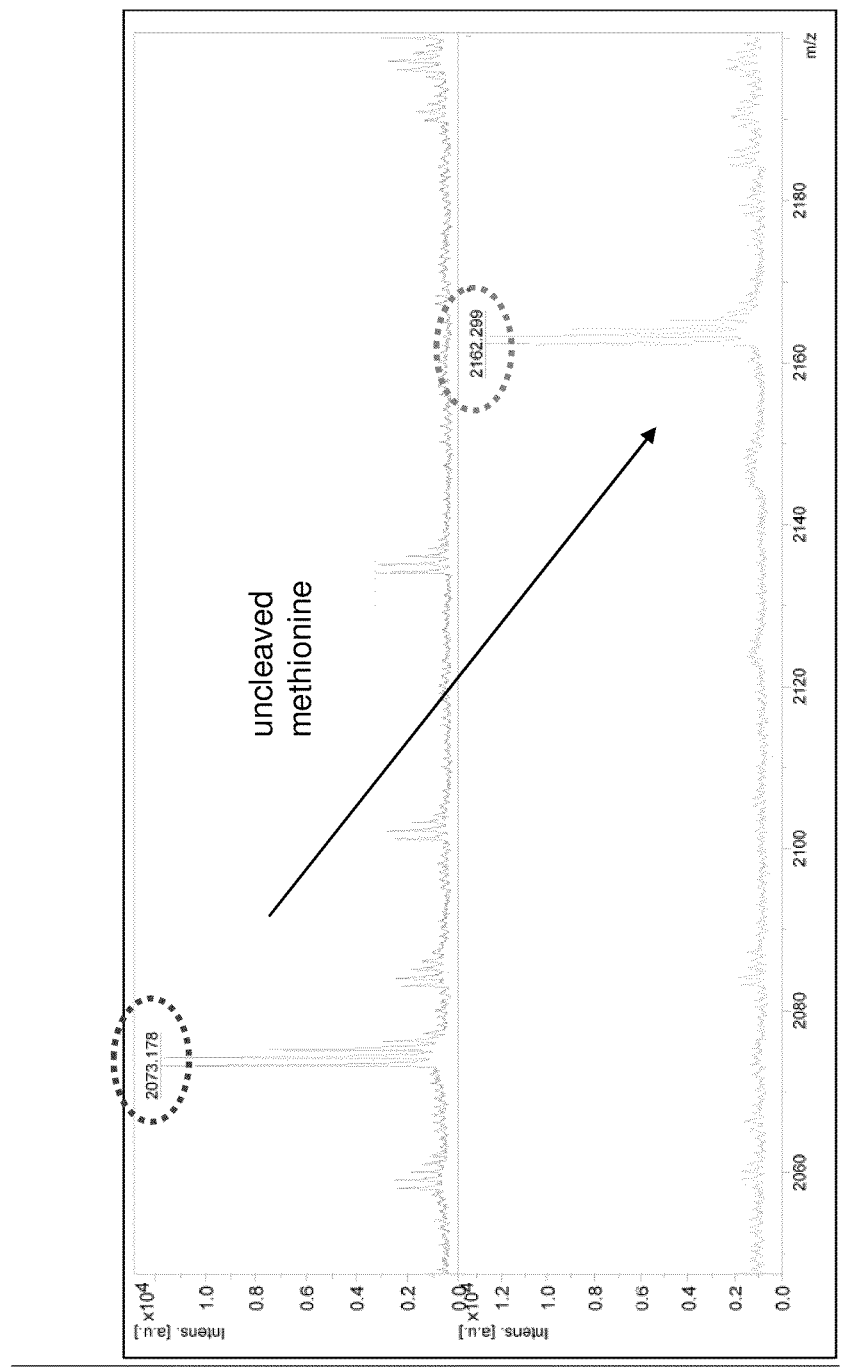

FIG. 5 shows the determination of N-terminus comprising the steps of: localization of N-terminal peptide, sequence determination by MSMS and characterization of N-terminal processing. The mass map of Band 1 corresponds to the sequence acGKEKTHINIVVIGHVDSGK (SEQ ID NO: 4) ($M+H^+$: 2.073.2); the mass map of Band 2 corresponds to the sequence MGKEKTHINIVVIGHVDSGK (SEQ ID NO: 5) ($M+H^+$: 2.162.2).

Figure 6:
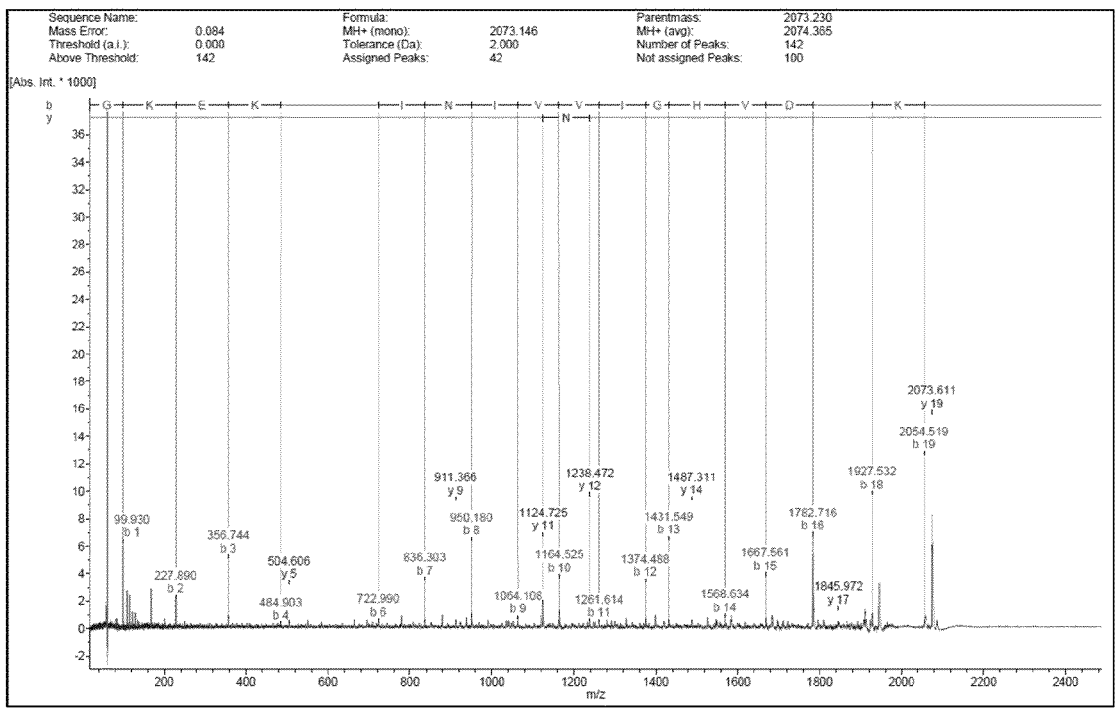

FIG. 6 shows the MSMS analysis of parent mass 2.073.2 D from the tryptic digest of the Band 1, which reveals the sequence acGKEKTHINIVVIGHVDSGK (SEQ ID NO: 4). FIG. 6 discloses "GKEK" as residues 1-4 of SEQ ID NO: 4 and "INIVVIGHVD" as residues 7-16 of SEQ ID NO: 4.

Figure 7:
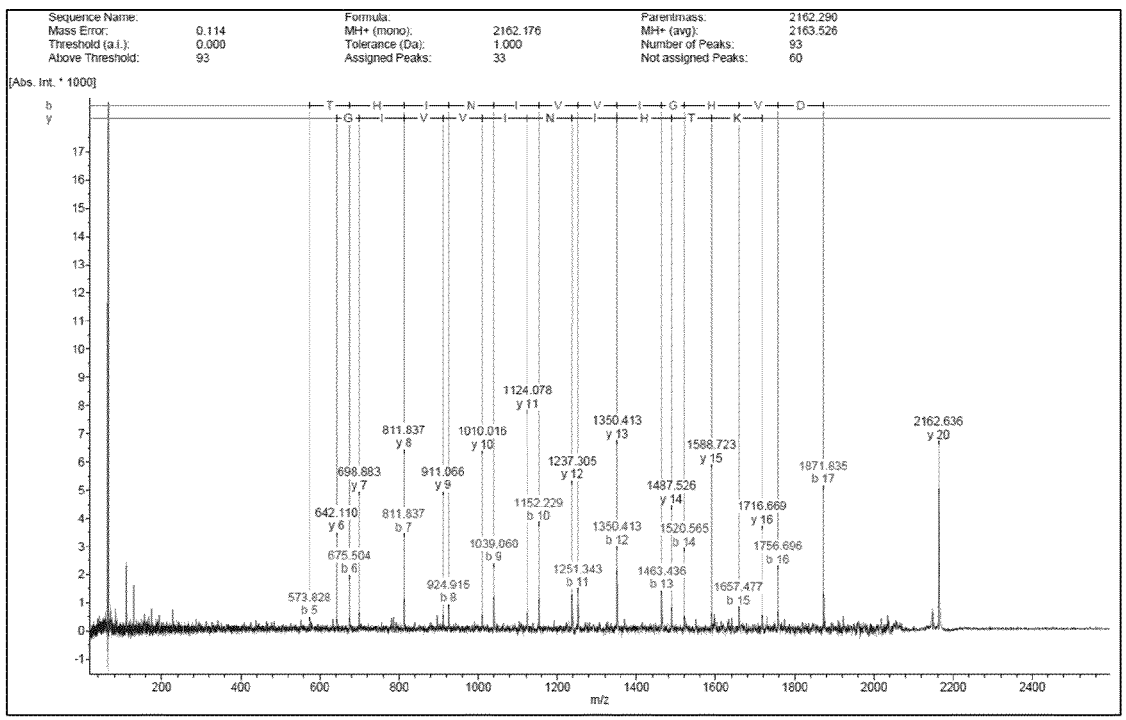

FIG. 7 shows the MSMS analysis of parent mass 2.162.2 D from the tryptic digest of the Band 2, which reveals the sequence MGKEKTHINIVVIGHVDSGK (SEQ ID NO: 5). FIG. 7 discloses "THINIVVIGHVD" as residues 6-17 of SEQ ID NO: 5 and "KTHINIVVIG" as residues 5-14 of SEQ ID NO: 5.

Figure 8:
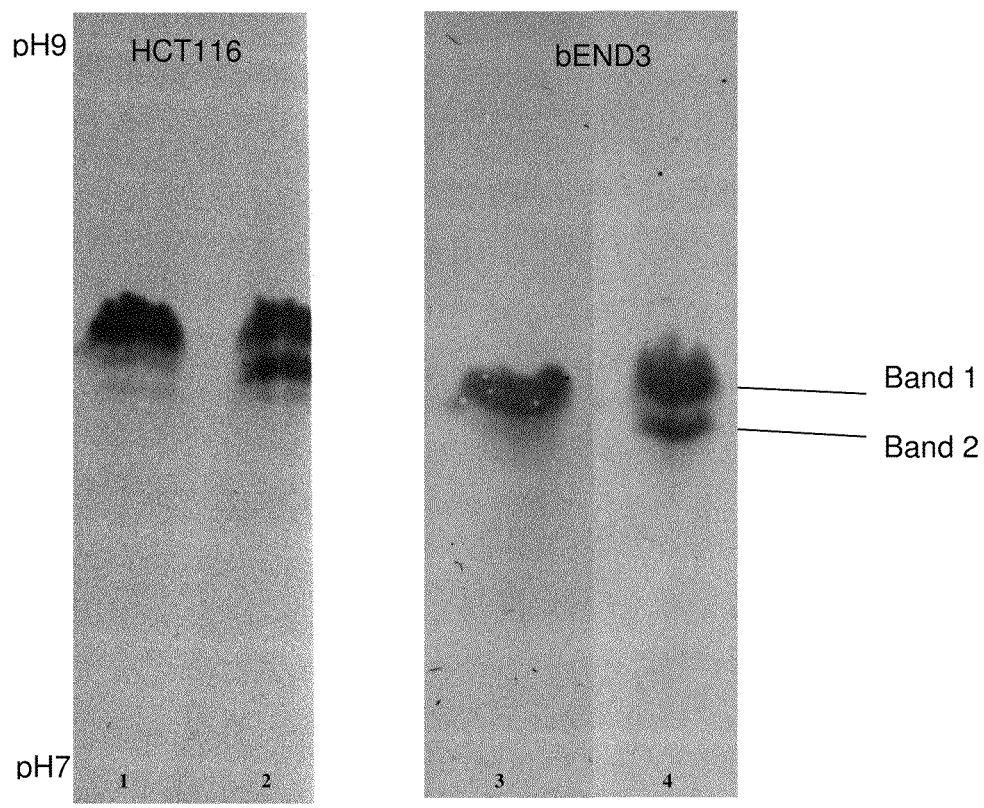

FIG. 8 shows the evaluation of the EEF1A1 identification for two cell extracts (lane 1, 3: DMSO; lane 2, 4: TNP470).

Figure 9:
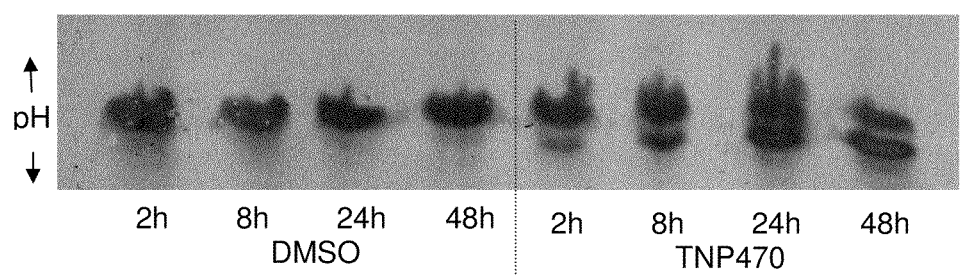

FIG. 9 shows the EEF1A1 mobility shift in bEND3 cell extracts treated with TNP470. No additional band occurred in the control sample (0.5% DMSO) after 48 h.

Figure 10:

FIG. 10 shows the EEF1A1 mobility shift with negative controls unequivocally distinguishable from active MetAP2 inhibitors (TNP-470, A-832234; lane 1-4: cf. Table 1).

FIG. 11 shows the sequence alignment of EEF1A1 (P68104; SEQ ID NO: 1) and EEF1A2 (Q05639; SEQ ID NO: 2), which has 92.7% sequence identity. Both accession numbers refer to the sequence database Swiss-Prot.

EXAMPLE 1

Treatment-Related Pattern Shows a New Band with Lower pI after IEF

Figure 1:
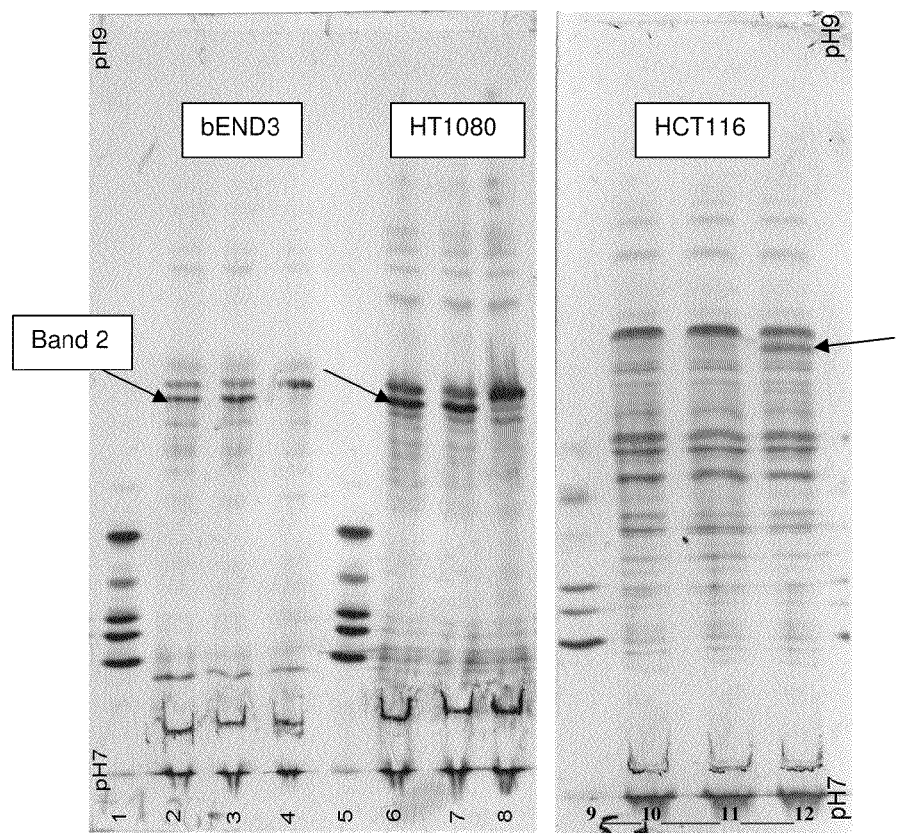
Figure 2:
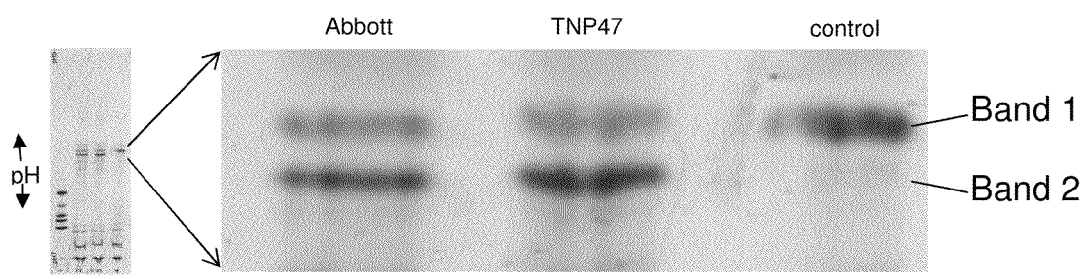
FIG. 2 shows a zoomed view for lanes 2-4 from FIG. 1.

IEF separation of cellular extracts after treatment of different endothelial and cancer cells (mouse: bEND3, human: HT1080, HCT116) was performed in a range of pH 7-9 (FIG. 1). Comparing extracts from DMSO-treated and MetAP2 inhibitor-treated (100 nM TNP-470; 1 µM 2-[2-((Z)-3-Di-ethylamino-propenyl)-4-fluoro-benzenesulfonylamino]-5,6,7,8-tetrahydro-naphthalene-1-carboxylic acid, which is identical to A-832234) cells, a novel protein band (FIG. 1, Band 2, see arrow) was detected after Coomassie Blue staining. A zoomed view is shown in FIG. 2.

EXAMPLE 2

Characterization of EEF1A1 by Edman Sequencing

Figure 3:
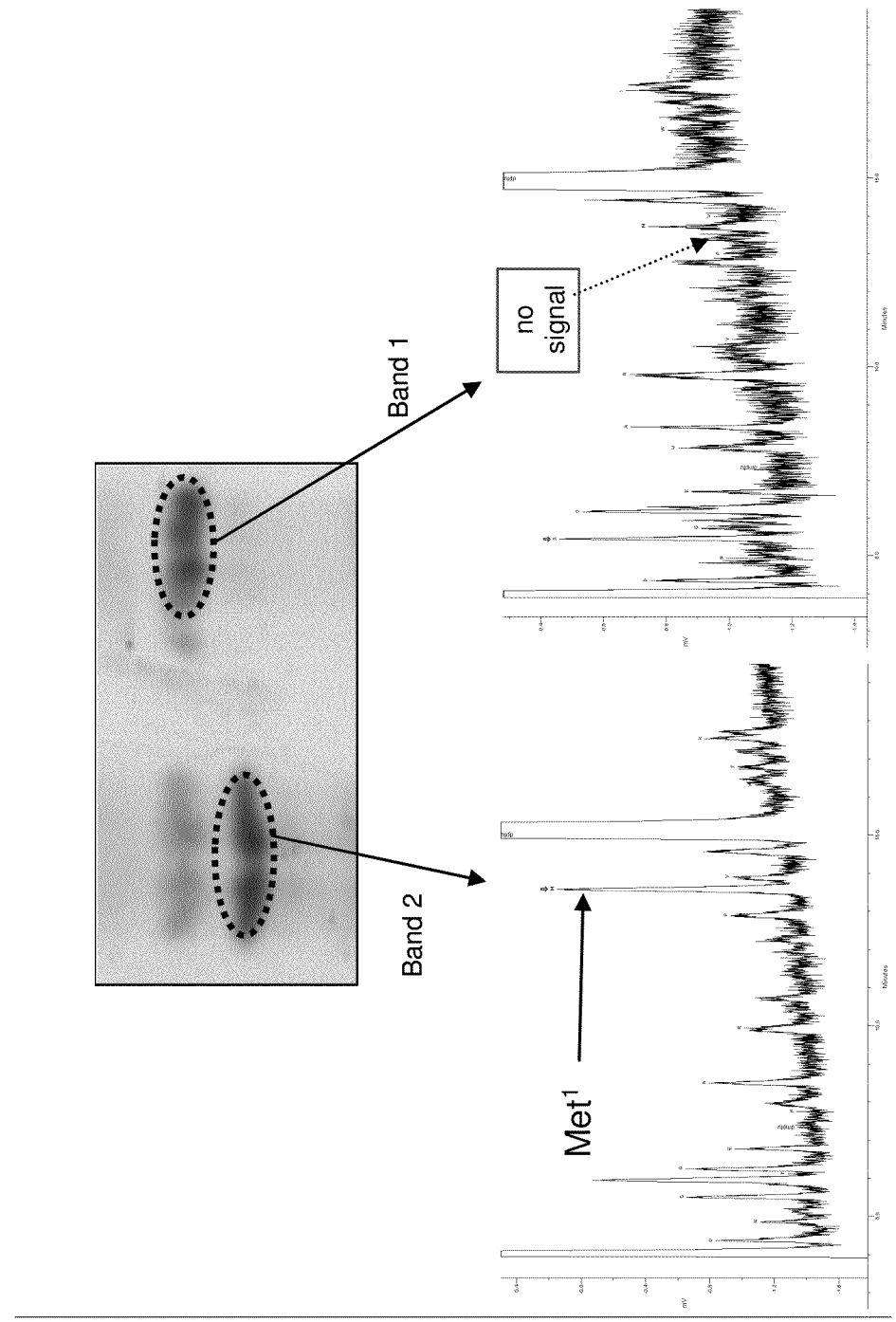
FIG. 3 shows the results of Edman sequencing that confirms $Met^1$ at the N-terminus of EEF1A1 after MetAP2 inhibition. Sequence detected for TNP470-treated HT1080+ bEND3 cells is $M^1$GKEKTHINI (SEQ ID NO: 3).

By N-terminal sequencing of the protein band as obtained in Example 1, the amino acid sequence MGKEKTHINI (SEQ ID NO: 3) was determined. A database sequence comparison identified the corresponding protein as EF1α for the Band 2 (FIG. 3). No amino acid signal was detected for the Band 1 which is typical for N-terminally blocked proteins.

EXAMPLE 3

Characterization of EEF1A1 by MS

Tryptic in gel digestion of the Band1 and Band 2 as obtained in Example 1 was applied for mass analysis. The corresponding mass lists also identified the protein EEF1A1 for both digests in the database search. This annotation was in agreement to the N-terminal sequencing result of the Band 2 (cf. Example 2, FIG. 3). The annotated tryptic peptides in respect to the EEF1A1 sequence are shown in FIG. 4.

Strikingly, comparison of both mass maps showed that each contained one differential peptide mass. The Band 2 contained a peptide at mw=2.162 D which was not present in the Band 1; for Band 1 a peptide at mw=2.073 D was exclusively detected (FIG. 5).

MS fragmentation of the peptide at mw=2.162 D identified the methionine-containing peptide MGKEKTHINIVVIGHVDSGK (FIG. 7) (SEQ ID NO: 5), and the peptide at mw=2.073 D identified the amino-terminally cleaved and acetylated form acGKEKTHINIVVIGH-VDSGK (FIG. 6) (SEQ ID NO: 4). This observation was in agreement with the occurrence of the Band 2 of EEF1A1 especially after treatment with TNP470.

EXAMPLE 4

Immunoanalysis Confirms the Identity of EEF1A1

Both bands as obtained in Example 1 were specifically detected using a polyclonal rabbit PcAb anti human EEF1A1 antibody which also cross-reacts with the mouse homolog. The evaluation of the EEF1A1 identification for two cell extracts is shown in FIG. 8.

EXAMPLE 5

Treatment-Related Mobility Shift is Independently Observed from the Cell Type

The EEF1A1 mobility shift could be reliably detected in all tested cell types with two structurally distinct MetAP2 inhibitors (TNP470) as it is shown in FIG. 9 (shown: bEND3 cell extract). No additional band occurred in the control sample even after 48 h, whereas a second band (Band 2) with increasing intensity was already to be seen after 2 h (FIG. 9). Negative controls were unequivocally distinguished from active compounds (FIG. 10; Table 1).

EXAMPLE 6

The two isoforms EEF1A1 and EEF1A2 comprise a sequence identity of 92.7% (FIG. 11). Both isoforms are identical within the first 82 amino acids and, therefore, are substrates of MetAP2.

TABLE 1

| Lane | Compound | Concentration [M] | Inhibition of MetAP2 activity [M] | Inhibition of HUVEC proliferation (BrdU incorporation) [M] |
|---|---|---|---|---|
| 1 | DMSO | | | |
| 2 | A-832234 | 1e−06 | 1e−08 | 7e−09 |
| 3 | TNP470 | 1e−07 | 1.4e−08 | 1e−10 |
| 4 | control | 1e−05 | 1.1e−06 | n.d. |

The invention claimed is:

1. A method for identifying a compound that has methionine aminopeptidase 2 (MetAP2)-dependent anti-proliferative activity, anti-angiogenic activity or anti-tumor activity, comprising
   (a) incubating a cellular system that expresses MetAP2 and eukaryotic translation elongation factor 1 alpha (EEF1A) with a compound that is exogenous in origin to the cellular system, wherein the system is selected from the group consisting of single cells, cell cultures, tissues, organs and mammals, and
   (b) directly detecting EEF1A with an N-terminal methionine residue (MetEEF1A) in a sample of the cellular system of step (a) and in a sample of a negative control system by use of isoelectric-focusing electrophoresis (IEF), optionally followed by Edman sequence analysis, or mass spectrometry,
   whereby a statistically significant increase in the presence of MetEEF1A in the test system as compared to the negative control system indicates that the N-terminal methionine of MetEEF1A is not cleaved in the test system by MetAP2, and the test compound is identified as having MetAP2 inhibitory activity, and
   (c) selecting the compound identified in (b) for further in vitro analysis.

2. The method of claim 1, further comprising detecting specific binding of said test compound to MetAP2 protein.

3. The method of claim 1, wherein the compound is being screened for therapeutic efficacy for a proliferative-driven disorder or condition, wherein the cellular system is a mammal, wherein the cellular system is incubated with the compound by administering the compound to the mammal, wherein the negative control system is the mammal before administration, and wherein a statistically significant increase in MetEEF1A in the sample from the mammal after administration as compared to the sample from the mammal before administration indicates a likelihood that the test compound is therapeutic.

4. The method of claim 1, wherein the mammal is non-human.

5. The method of claim 1, wherein the compound selectively inhibits MetAP2 as compared to MetAP1.

* * * * *

SEQUENCE LISTING

<160> NUMBER OF SEQ ID NOS: 5

<210> SEQ ID NO 1
<211> LENGTH: 462
<212> TYPE: PRT
<213> ORGANISM: Homo sapiens

<400> SEQUENCE: 1

```
Met Gly Lys Glu Lys Thr His Ile Asn Ile Val Val Ile Gly His Val
1               5                   10                  15

Asp Ser Gly Lys Ser Thr Thr Thr Gly His Leu Ile Tyr Lys Cys Gly
            20                  25                  30

Gly Ile Asp Lys Arg Thr Ile Glu Lys Phe Glu Lys Glu Ala Ala Glu
        35                  40                  45

Met Gly Lys Gly Ser Phe Lys Tyr Ala Trp Val Leu Asp Lys Leu Lys
50                  55                  60

Ala Glu Arg Glu Arg Gly Ile Thr Ile Asp Ile Ser Leu Trp Lys Phe
65                  70                  75                  80

Glu Thr Ser Lys Tyr Tyr Val Thr Ile Ile Asp Ala Pro Gly His Arg
                85                  90                  95

Asp Phe Ile Lys Asn Met Ile Thr Gly Thr Ser Gln Ala Asp Cys Ala
                100                 105                 110

Val Leu Ile Val Ala Ala Gly Val Gly Glu Phe Glu Ala Gly Ile Ser
            115                 120                 125

Lys Asn Gly Gln Thr Arg Glu His Ala Leu Leu Ala Tyr Thr Leu Gly
130                 135                 140

Val Lys Gln Leu Ile Val Gly Val Asn Lys Met Asp Ser Thr Glu Pro
145                 150                 155                 160

Pro Tyr Ser Gln Lys Arg Tyr Glu Glu Ile Val Lys Glu Val Ser Thr
                165                 170                 175

Tyr Ile Lys Lys Ile Gly Tyr Asn Pro Asp Thr Val Ala Phe Val Pro
                180                 185                 190

Ile Ser Gly Trp Asn Gly Asp Asn Met Leu Glu Pro Ser Ala Asn Met
            195                 200                 205

Pro Trp Phe Lys Gly Trp Lys Val Thr Arg Lys Asp Gly Asn Ala Ser
210                 215                 220

Gly Thr Thr Leu Leu Glu Ala Leu Asp Cys Ile Leu Pro Pro Thr Arg
225                 230                 235                 240

Pro Thr Asp Lys Pro Leu Arg Leu Pro Leu Gln Asp Val Tyr Lys Ile
                245                 250                 255

Gly Gly Ile Gly Thr Val Pro Val Gly Arg Val Glu Thr Gly Val Leu
                260                 265                 270

Lys Pro Gly Met Val Val Thr Phe Ala Pro Val Asn Val Thr Thr Glu
            275                 280                 285

Val Lys Ser Val Glu Met His His Glu Ala Leu Ser Glu Ala Leu Pro
290                 295                 300

Gly Asp Asn Val Gly Phe Asn Val Lys Asn Val Ser Val Lys Asp Val
305                 310                 315                 320

Arg Arg Gly Asn Val Ala Gly Asp Ser Lys Asn Asp Pro Pro Met Glu
                325                 330                 335

Ala Ala Gly Phe Thr Ala Gln Val Ile Ile Leu Asn His Pro Gly Gln
                340                 345                 350

Ile Ser Ala Gly Tyr Ala Pro Val Leu Asp Cys His Thr His Ile
            355                 360                 365

Ala Cys Lys Phe Ala Glu Leu Lys Glu Lys Ile Asp Arg Arg Ser Gly
370                 375                 380

Lys Lys Leu Glu Asp Gly Pro Lys Phe Leu Lys Ser Gly Asp Ala Ala
385                 390                 395                 400

Ile Val Asp Met Val Pro Gly Lys Pro Met Cys Val Glu Ser Phe Ser
```

```
                        405                 410                 415
Asp Tyr Pro Pro Leu Gly Arg Phe Ala Val Arg Asp Met Arg Gln Thr
            420                 425                 430

Val Ala Val Gly Val Ile Lys Ala Val Asp Lys Lys Ala Ala Gly Ala
            435                 440                 445

Gly Lys Val Thr Lys Ser Ala Gln Lys Ala Gln Lys Ala Lys
            450                 455                 460

<210> SEQ ID NO 2
<211> LENGTH: 463
<212> TYPE: PRT
<213> ORGANISM: Homo sapiens

<400> SEQUENCE: 2

Met Gly Lys Glu Lys Thr His Ile Asn Ile Val Val Ile Gly His Val
1               5                   10                  15

Asp Ser Gly Lys Ser Thr Thr Thr Gly His Leu Ile Tyr Lys Cys Gly
            20                  25                  30

Gly Ile Asp Lys Arg Thr Ile Glu Lys Phe Glu Lys Glu Ala Ala Glu
        35                  40                  45

Met Gly Lys Gly Ser Phe Lys Tyr Ala Trp Val Leu Asp Lys Leu Lys
    50                  55                  60

Ala Glu Arg Glu Arg Gly Ile Thr Ile Asp Ile Ser Leu Trp Lys Phe
65                  70                  75                  80

Glu Thr Thr Lys Tyr Tyr Ile Thr Ile Asp Ala Pro Gly His Arg
                85                  90                  95

Asp Phe Ile Lys Asn Met Ile Thr Gly Thr Ser Gln Ala Asp Cys Ala
            100                 105                 110

Val Leu Ile Val Ala Ala Gly Val Gly Glu Phe Glu Ala Gly Ile Ser
        115                 120                 125

Lys Asn Gly Gln Thr Arg Glu His Ala Leu Leu Ala Tyr Thr Leu Gly
    130                 135                 140

Val Lys Gln Leu Ile Val Gly Val Asn Lys Met Asp Ser Thr Glu Pro
145                 150                 155                 160

Ala Tyr Ser Glu Lys Arg Tyr Asp Glu Ile Val Lys Glu Val Ser Ala
                165                 170                 175

Tyr Ile Lys Lys Ile Gly Tyr Asn Pro Ala Thr Val Pro Phe Val Pro
            180                 185                 190

Ile Ser Gly Trp His Gly Asp Asn Met Leu Glu Pro Ser Pro Asn Met
        195                 200                 205

Pro Trp Phe Lys Gly Trp Lys Val Glu Arg Lys Glu Gly Asn Ala Ser
    210                 215                 220

Gly Val Ser Leu Leu Glu Ala Leu Asp Thr Ile Leu Pro Pro Thr Arg
225                 230                 235                 240

Pro Thr Asp Lys Pro Leu Arg Leu Pro Leu Gln Asp Val Tyr Lys Ile
                245                 250                 255

Gly Gly Ile Gly Thr Val Pro Val Gly Arg Val Glu Thr Gly Ile Leu
            260                 265                 270

Arg Pro Gly Met Val Val Thr Phe Ala Pro Val Asn Ile Thr Thr Glu
        275                 280                 285

Val Lys Ser Val Glu Met His His Glu Ala Leu Ser Glu Ala Leu Pro
    290                 295                 300

Gly Asp Asn Val Gly Phe Asn Val Lys Asn Val Ser Val Lys Asp Ile
305                 310                 315                 320
```

```
Arg Arg Gly Asn Val Cys Gly Asp Ser Lys Ser Asp Pro Pro Gln Glu
            325                 330                 335

Ala Ala Gln Phe Thr Ser Gln Val Ile Ile Leu Asn His Pro Gly Gln
            340                 345                 350

Ile Ser Ala Gly Tyr Ser Pro Val Ile Asp Cys His Thr Ala His Ile
            355                 360                 365

Ala Cys Lys Phe Ala Glu Leu Lys Glu Lys Ile Asp Arg Arg Ser Gly
            370                 375                 380

Lys Lys Leu Glu Asp Asn Pro Lys Ser Leu Lys Ser Gly Asp Ala Ala
385                 390                 395                 400

Ile Val Glu Met Val Pro Gly Lys Pro Met Cys Val Glu Ser Phe Ser
                405                 410                 415

Gln Tyr Pro Pro Leu Gly Arg Phe Ala Val Arg Asp Met Arg Gln Thr
            420                 425                 430

Val Ala Val Gly Val Ile Lys Asn Val Glu Lys Lys Ser Gly Gly Ala
            435                 440                 445

Gly Lys Val Thr Lys Ser Ala Gln Lys Ala Gln Lys Ala Gly Lys
            450                 455                 460
```

<210> SEQ ID NO 3
<211> LENGTH: 10
<212> TYPE: PRT
<213> ORGANISM: Homo sapiens

<400> SEQUENCE: 3

```
Met Gly Lys Glu Lys Thr His Ile Asn Ile
1               5                   10
```

<210> SEQ ID NO 4
<211> LENGTH: 19
<212> TYPE: PRT
<213> ORGANISM: Homo sapiens
<220> FEATURE:
<223> OTHER INFORMATION: N-term acetylated

<400> SEQUENCE: 4

```
Gly Lys Glu Lys Thr His Ile Asn Ile Val Val Ile Gly His Val Asp
1               5                   10                  15

Ser Gly Lys
```

<210> SEQ ID NO 5
<211> LENGTH: 20
<212> TYPE: PRT
<213> ORGANISM: Homo sapiens

<400> SEQUENCE: 5

```
Met Gly Lys Glu Lys Thr His Ile Asn Ile Val Val Ile Gly His Val
1               5                   10                  15

Asp Ser Gly Lys
            20
```